(12) United States Patent
El-Hibri et al.

(10) Patent No.: US 9,345,812 B2
(45) Date of Patent: *May 24, 2016

(54) MEDICAL TUBINGS MADE OF A POLYMER MATERIAL

(71) Applicant: SOLVAY ADVANCED POLYMERS, L.L.C., Alpharetta, GA (US)

(72) Inventors: Mohammad Jamal El-Hibri, Atlanta, GA (US); Brian Baleno, Alpharetta, GA (US); Nikica Maljkovic, New Orleans, LA (US); Bianca Sadicoff Shemper, Hattiesburg, MS (US); Jean-Baptiste Bonnadier, Atlanta, GA (US); Daniel J. Ireland, Kernersville, NC (US); Henri N. J. Massilon, Waremme (BE)

(73) Assignee: SOLVAY SPECIALTY POLYMERS USA, LLC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/262,225

(22) Filed: Apr. 25, 2014

(65) Prior Publication Data

US 2014/0236101 A1    Aug. 21, 2014

Related U.S. Application Data

(60) Division of application No. 12/764,684, filed on Apr. 21, 2010, now Pat. No. 8,742,064, and a continuation-in-part of application No. PCT/EP2008/064349, filed on Oct. 23, 2008, and a continuation-in-part of application No. 12/206,825, filed on Sep. 9, 2008, now Pat. No. 8,119,764.

(60) Provisional application No. 61/314,613, filed on Mar. 17, 2010, provisional application No. 60/981,874, filed on Oct. 23, 2007, provisional application No. 60/982,193, filed on Oct. 24, 2007.

(30) Foreign Application Priority Data

Mar. 29, 2010   (EP) .................................. 10158123

(51) Int. Cl.
| | |
|---|---|
| *C08G 61/10* | (2006.01) |
| *C08G 16/00* | (2006.01) |
| *C08G 16/06* | (2006.01) |
| *A61L 31/04* | (2006.01) |
| *A61L 29/06* | (2006.01) |
| *A61L 31/06* | (2006.01) |
| C08F 283/08 | (2006.01) |
| C08F 283/00 | (2006.01) |
| C08L 65/02 | (2006.01) |

(52) U.S. Cl.
CPC ............. *A61L 31/048* (2013.01); *A61L 29/06* (2013.01); *A61L 31/06* (2013.01); *C08G 61/10* (2013.01); *A61L 2300/80* (2013.01); *C08G 2261/314* (2013.01); *C08L 65/02* (2013.01)

(58) Field of Classification Search
CPC ...................................................... C08G 61/10
USPC ................... 528/396, 220, 127, 128; 525/534; 424/9.322; 264/45.9, 319; 604/264
See application file for complete search history.

(56) References Cited

U.S. PATENT DOCUMENTS 8,119,764 B2 * 2/2012 Maljkovic et al. ............ 528/396
8,742,064 B2 * 6/2014 El-Hibri et al. ............... 528/396

* cited by examiner

*Primary Examiner* — Duc Truong

(57) ABSTRACT

Medical tubing (T), such as a guidewire, a stent, a catheter or a hollow needle, made of a kinked rigid-rod polyarylene exhibiting a outstanding characteristics including high torqueability, high pushability and high flexibility and which can be easily thin-wall extruded under especially harsh conditions.

6 Claims, 2 Drawing Sheets

MEDICAL TUBINGS MADE OF A POLYMER MATERIAL

REFERENCE TO RELATED APPLICATIONS

This application is a division of U.S. application Ser. No. 12/764,684, filed Apr 24, 2010 now U.S. Pat. No. 8,742,064, which (1) claims the benefit under 35 U.S.C. §119(e) of U.S. provisional application No. 61/314,613 filed Mar. 17, 2010, (2) claims the benefit under 35 U.S.C. §119(a) of EP application No. 10158123.9 filed Mar. 29, 2010, and (3) is a continuation-in-part of PCT application no. PCT/EP2008/064349 filed Oct. 23, 2008, which (A) claims the benefit under 35 U.S.C. §119(e) of U.S. provisional application No. 60/981,874 filed Oct. 23, 2007, (B) claims the benefit under 35 U.S.C. §119(e) of U.S. provisional application No. 60/982,193 filed Oct. 24, 2007, and (C) is a continuation-in-part of U.S. application Ser. No. 12/206,825 filed Sep. 9, 2008. The entire contents of each of these applications are explicitly incorporated herein by this reference.

FIELD OF THE INVENTION

The present invention relates to medical tubings made of a particular polymer material.

BACKGROUND OF THE INVENTION

Medical tubings are made from a variety of materials. Glass, metal and polymers are used in a variety of medical applications. They are generally sterilized and small in diameter. Some medical tubings feature diameters that measure thousandths of an inch, with walls thinner than a human hair. These small, specialty tubes can cost many times more than conventional high-volume tubes, but are well-suited for catheters and other medical devices that are inserted into a patient's cardiovascular system. In general, medical tubing manufacturers seek to reduce the outside diameter of their tubings while maintaining as large an inside diameter as possible; tubes with larger inside diameters provide doctors and other medical personnel with more room to insert tools or deliver drugs.

Important specifications for medical tubings include not only outside diameter and inside diameter, but also wall thickness. To produce medical tubings with extremely thin walls, manufacturers force material to flow through the small orifices of processing equipment. Gear or melt pumps are often used in the extrusion of very small tubes. Aiming at minimizing flow problems, some manufacturers use special materials for thin-wall extrusion. Examples thereof include polyether block amides, which are plasticizer-free thermoplastic elastomers that are often used in catheter tubing for angiographies, angioplasties, endoscopies, and biopsies. The problem is that, in many instances, such special materials do not exhibit the desired balance of properties; in particular, they provide medical tubing exhibiting a low rigidity, and additional reinforcement is then needed.

It has already been attempted to gain in rigidity by producing multilayer tubings that include reinforcements made from layers of different materials. Typically, tubings are extruded and braided over with a wire or a highly rigid polymer composition. Methods for producing multilayer tubings are by essence more complex, and further, the different layers are subject to delamination.

WO 2005/102406 (to Boston Scientific Scimed) and WO 2006/037078 (to Cordis Corp.), the whole content of which is herein incorporated by reference, describe medical devices, such as catheters, made from certain rigid-rod poly(1,4-phenylene)s, as developed by Mississipi Polymer Technology under the trademark Parmax® SRP (SRP for "Self-Reinforcing Polymers"). The so-produced medical tubings are supposed to include high compression and flexural strength without reinforcing agent, as well as high chemical and wear resistance, non combustibility, high corrosion resistance, high scratch resistance, and very low moisture absorption. Unfortunately, because of the intrinsic nature of the so-proposed rigid-rod polyparaphenylene, extruding it into catheters and other medical tubings with extremely thin walls is extremely difficult; in practice, such rigid-rod polyphenylene need to be solvent-casted into thin films from various solvent mixtures, such as NMP, with all the economic and environmental drawbacks linked to the use of solvents. Further, the torqueability and the flexibility of medical tubings made of rigid-rod poly(1,4-phenylene)s may be not as high as it would be desirable for certain applications.

Very small diameter medical tubings with very thin walls can be difficult to extrude through a standard extrusion head/die. Oftentimes, the viscosity of these materials in the die is so high and the die gap is so small that one must increase the temperature of the polymer in order to reduce the viscosity of the material so that they can get sufficient flow through the die. This practice can dramatically alter material properties. When extruding thin-walled tubing, specially designed heads are often required to produce high quality tubing without degradation, gels, black specs, or undesirable residual stress.

Many custom extruders have already tried to overcome the problems of producing tight tolerance, small diameter thin walled tubing by using high draw down ratios. This significantly improves dimensional tolerances, increases line speed and makes tooling much easier to fabricate. Unfortunately, running high draw down ratios also imparts significant orientation and residual stress/strain in the finished tubing. This orientation can significantly increase the tensile strength and reduce the elongation of the tubing in the machine direction. It can also reduce the tubing burst pressure due to the loss in hoop strength. The residual stresses from high drawn down ratios can wreak havoc during subsequent thermal processing, sterilization, or aging (natural or accelerated). These thermal processes can release the stresses built in during extrusion, causing the tubing to shrink significantly in length and increase in diameter and wall thickness.

The process used to produce medical tubing can thus be extremely important in high end diagnostic and therapeutic catheters where market pressures have driven tubing manufacturers to design smaller and smaller devices with thinner and thinner walls for end use applications where the mechanical, physical, chemical, electrical, or thermal properties are critical to the function of the finished medical tubings.

There is a need for medical tubings exhibiting a confluence of characteristics including high torqueability, high pushability and high flexibility, as well as all the above other listed beneficial properties of the rigid-rod poly(1,4-phenylene)s, and which can be easily thin-wall extruded under especially harsh conditions (e.g. by using an extruder with extremely small orifices).

Further, thin-walled tubings exhibiting the above confluence of characteristics could find useful applications in many other fields than the medical field, in particular building and automotive applications.

Hollow needles form a class of tubings of particular interest. Hollow needles are used in a variety of applications. Medical, surgical and cosmetic hollow needles are broadly used to penetrate into a human or animal body. Metal and metal alloys, especially stainless steel, has been for several decades the material of choice for hollow needles.

Stainless steel hollow needles have been appreciated for their high compression and flexural strength, high rigidity, high stiffness, high surface hardness, high ductility, high impact resistance, high chemical resistance, high corrosion resistance, non combustibility, low moisture absorption, good ability to hold a sharp edge and penetrability.

The penetrability of a needle can be defined as the ability or easiness for a needle to penetrate in a suitable manner into a substrate such as a skin or a vein; upon penetration, the hollow needle should neither break nor endorse a substantial deformation; it should not tear up in any manner the substrate that is penetrated (esp. it should not rip up the flesh). Further, needles for injection into human or animal tissue have to be terminated by a sharp edge (also named, point) and to be very small in diameter in order to limit the pain experienced by the patient, whilst retaining adequate penetrability of the skin, vein, muscle or the like.

As the skilled person will easily understand, this property is key for a hollow needle and is essentially specific to this end use. Insofar as the Applicant knows, it is extremely difficult to predict what the penetrability of a needle is based on more familiar properties of the material the needle is made of. Besides, without being bound to any theory, the Applicant is of the opinion that achieving the right penetrability likely requires a subtle and unelucidated balance of properties, among which it could possibly be cited among others high compression and flexural strength and high rigidity on one hand, and high ductility and a high impact resistance on the other hand; the penetrability depends further on the design of the hollow needle, including its length, aspect ratio and, last but not least, the sharpness of its edge.

With this regard, the ability to hold a sharp edge is another key property for a hollow needle. Indeed, this property does not only improve the penetrability of the hollow needle as above explained, but it also contributes as such to decrease or relieve the pain felt by a patient (or more generally by a human or an animal) when the needle penetrates and possibly goes through its skin, vein, muscle or other surface layer. As the skilled person will easily appreciate, it is also essentially specific to needle end uses. The Applicant is not aware of any study that would have addressed so far the question of the ability for a needle to hold a sharp edge as function of the chemical nature of the plastic material the needle would have been made of. Finally, to the best of the Applicant's knowledge, it is also extremely difficult to predict the ability of a needle to hold a sharp edge, relying on more familiar properties of the material the needle is made of. Finally, without being bound to any theory, the Applicant is of the opinion that the ability for a needle to hold a sharp edge likely requires a complex and obscure balance of properties, among which it could possibly be cited among others a high compression and flexural strength and a high rigidity on one hand, and a high stiffness and a high surface hardness on the other hand; it depends further on the machinability of the material the needle is made of, in particular of the melt processability of the plastic material in case of plastic needles.

Because of this confluence of properties, the hollow needles of the prior art have been generally made of metal. However, metal hollow needles, once they have been used, cannot be easily disposed of, and this gives rise to a sanitary health problem because of contamination accidents arising from contact with or accidental re-utilization of thereof. Indeed, while a hollow needle, such as a medical, surgical or cosmetic needle, can be manufactured under sterile and apyrogenic conditions, and can be kept sterile and apyrogenic in its original pack, once it has been taken out from its pack and utilized, it cannot obviously be held anymore as sterile and apyrogenic.

There is a strong need for single-use, easily disposable hollow needles. This need is immediately apparent when thinking about applications such as mass vaccinations in Third-World countries which are not or poorly equipped with facilities allowing for re-sterilizing or depyrogenizing hypodermic needles that have already been used. Also, even in countries equipped with such facilities, re-sterilization and depyrogenization remain a tedious, time-consuming and complex processes, and, in general, it is also difficult to find reconditioning installations that would provide the same level of health safety as high as those offered by those achieving the original conditioning of the needles.

Another problem commonly associated with metal hollow needles results in the rather poor machinability of the metal, which problem is particularly acute when needles terminated by an extremely sharp edge have to be machined, as required by certain applications in the medical field.

There is thus also a need for hollow needles which can be machined more easily, including when the needles have an extremely sharp edge.

In order to solve the problem of providing single-use, easily disposable, easily machinable needles suitable for penetrating into the human body and able to hold a sharp edge, needles made of certain plastic materials have been proposed.

JP 7 303 700, the whole content of which is herein incorporated by reference for all purposes, describes a synthetic resin needle reinforced with combustible fibers whose longitudinal directions are arrayed straight or curvilinearly along the axial length of the needle. JP'700 proposes a wide variety of resins for making the reinforced synthetic needle. According to JP'700, the resin can be notably a thermoplastic resin, such as a polyphenylene sulfide, a polyetheretherketone, a polybutyleneterephthalate, a polycarbonate, a polyamide, a polyacetal, a modified polyphenylene ether, a polyester system resin, a polytetrafluoroethylene, a fluororesin, a polysulfone, a polyetherimide, a polyethersulfone, a polyetherketone, a polyetherlactone, a liquid crystal polyester, a polyamideimide, a polyimide or a polyethernitrile, a polypropylene, a polyethylene or a cyclic olefin system resin; it can also be a thermoset resin such as an epoxy resin, an unsaturated polyester resin, a phenol resin, a urea resin, a melamine resin or a polyurethane resin.

US 2004/199127, the whole content of which is herein incorporated by reference, describes a process for the manufacture of a plastic injection needle in which the employed plastic is a liquid crystalline polyester comprising 70-80 percent hydroxybenzoic acid and 20-30 percent hydroxynaphthoic acid. The plastic needle of US 2004/199127 preferably further comprises from 15 to 40 percent by weight of the solid plastic of fiber reinforcement such as glass fiber or carbon fiber or aramid fiber.

While easily disposable, the needles U.S. Pat. No. '127 which are made of unreinforced liquid crystalline polyester have not the suitable confluence of properties achieved by metal needles, lacking notably in compression and flexural strength, rigidity, penetrability and ability to hold a sharp edge. By the way, exactly the same drawbacks would apply to needles that would have been made of unreinforced polymer material based on any of the synthetic resins described in JP'700, in particular based on polyetheretherketone (PEEK).

Likewise, the needles U.S. Pat. No. '127 which are made of reinforced liquid crystalline polyester and, more generally, the needles of JP'700 which can be made of a variety of other reinforced synthetic resins, have not the suitable confluence of properties achieved by metal needles, lacking notably in ductility, impact resistance, penetrability and ability to hold a sharp edge; the reinforcing agent present in the synthetic resin matrix limits also substantially the possibilities of subsequent recycling of the polyester material.

US 2007/073249, the whole content of which is herein incorporated by reference, describes a needle constituted of a cylindrical body extended along a longitudinal axis, said body being made of a polyaryletherketone polymer (such as PEEK) and further comprising metal reinforcement wires embedded in the polyaryletherketone polymer, extending parallel to the longitudinal axis and distributed according to a particular design. The composite needle of U.S. Pat. No. '249 is not easily disposable because of the metal reinforcement wires embedded in the polymer matrix. The composite needle of U.S. Pat. No. '249 is more difficult to manufacture than a simple plastic or a metal needle. In addition, meeting a suitable confluence of properties with such a composite needle requires also more subtle adjustments, depending further notably on amount, dimensions, shape and positioning of the metal wires.

There are still other reasons making it extremely difficult to find a plastic material that could suitably replace metal for numbers of hollow needle applications.

As already mentioned, hollow needles often have thin walls, which can makes it difficult to mold a plastic material in a standard mold, or to extrude a plastic material through a standard extrusion head/die. Oftentimes, the viscosity of these materials in the die is so high that one must increase the temperature of the polymer in order to reduce the viscosity of the material so that they can get sufficient flow in the orifices of the mold or through the die. This practice can dramatically alter material properties. Hence, plastic materials suitable for making needles must demonstrate a good thermal stability and good melt processability.

Then, hollow needles used to penetrate into a human or animal body, must be non toxic and non irritant. They should not elicit any adverse host reactions to their contact, and, more generally, they should cause no injurious effect on the part of the body the are put in contact with. This further requires the plastic material to demonstrate excellent biocompatibility features.

There is a need for hollow needles, in particular medical and surgical needles, exhibiting a confluence of characteristics including high compression and flexural strength, high rigidity, high stiffness, high surface hardness, high ductility, high impact resistance, high chemical resistance, high corrosion resistance, non combustibility and low moisture absorption.

There is a need for hollow needles having a good penetrability.

There is a need for hollow needles having a good ability to hold a sharp edge.

There is a need for hollow needles that are non toxic. There is a need for hollow needles that are non irritant. There is a need for hollow needles that are biocompatible.

There is a need for easily disposable hollow needles, which would then be especially well suited for a single-use. There is a need for hollow needles made from a material exhibiting a good disposability and recyclability.

There is a need for hollow needles made from an easily machinable material. There is a need for hollow needles made of an easily melt processable and thermally stable material.

SUMMARY OF THE INVENTION

The present invention concerns a medical tubing (T) comprising at least one part consisting of a polymer material (M) comprising at least one kinked rigid-rod polyarylene (P) of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix (M) consisting of:

between 0 and 75 mole %, based on the total number of moles of the recurring units (R), of rigid rod-forming arylene units (Ra), said rigid rod-forming arylene units (Ra) being optionally substituted by at least one monovalent substituting group, with between 25 and 100 mole %, based on the total number of moles of the recurring units (R), of kink-forming arylene units (Rb), said kink-forming arylene units (Rb) medical tubing (T) being optionally substituted by at least one monovalent substituting group.

BRIEF DESCRIPTION OF THE DRAWINGS

The invention may be more completely understood in consideration of the following detailed description of various embodiments of the invention in connection with the accompanying drawings in which.

DETAILED DESCRIPTION OF THE INVENTION

The Medical Tubing (T)

Figure 1:
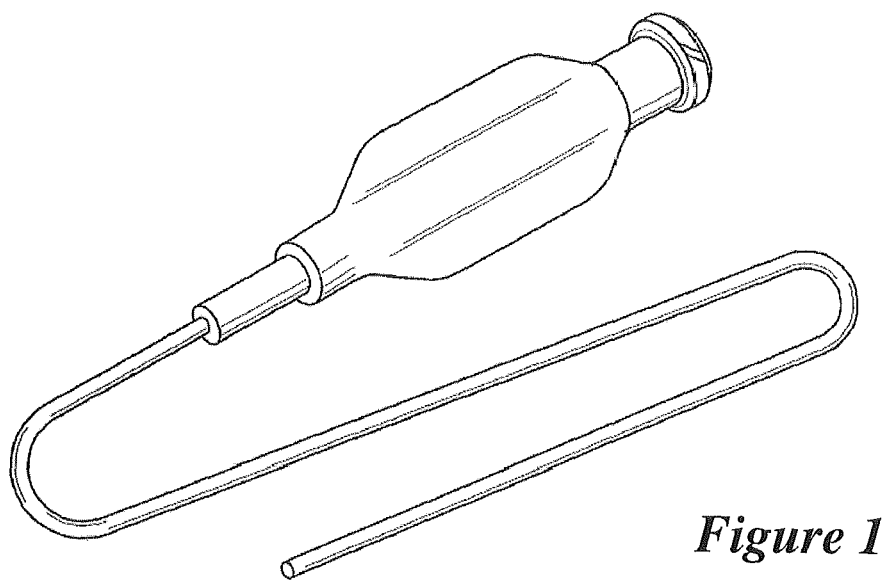
FIG. 1 depicts a diagnostic catheter or a guiding catheter in accordance with the present invention.

The term "tubing" is used in its broadest sense, to encompass any structure arranged at a radial distance around a longitudinal axis. Tubings, and in particular the tubings according to the present invention, are generally used for the conveyance of fluid, gas and sometimes other medium.

Accordingly, the term "tubing" includes any structure that (i) has a hollow cylinder form with a circular inner cross-section or not, such as for example an elliptical or polygonal inner cross-section, or any other regular or irregular cross-section; (ii) has a different or changing inner or outer cross-section along its length; (iii) is arranged around a straight, curving, bent or discontinuous longitudinal axis; (iv) has an imperforate surface, or a periodic or other perforate, irregular or gapped surface or cross-section; (v) is spaced uniformly or irregularly, including being spaced varying radial distances from the longitudinal axis; and/or (vi) has any desired combination of length or cross-sectional size.

Most specifications for medical tubing (T) consist advantageously of a drawing of a tube with the material, dimensions and tolerances. The medical tubing (T) according to the present invention features advantageously a single lumen. For single lumen tubings, the dimensions will usually include two of the following three dimensions; inner diameter (ID), outer diameter (OD) and the tubing wall thickness, along with their associated tolerances. In addition, the tubing length and tolerance is typically included unless the tubing is to be provided in a continuous length on a spool. Other notes that may appear on a tubing specification include packaging requirements; a sampling plan for inspection of the dimensional tolerances listed above; and some note regarding tubing cleanliness such as "no dirt, grease, oil, etc. to be present on the tubing surface". Very few specifiers of medical tubing specify other tubing attributes or process parameters associated with the production of the tubing. It is a common misconception that as long as a lot of tubing is made from the right material and meets the dimensional requirements, it will be the same as, or it is equivalent to, another lot of tubing either made by the same supplier or potentially made by a different supplier. While this may be true, there is also a good chance that the two lots of tubing may be different. These differences are not always obvious or easily recognizable, even when inspected by incoming QC. Oftentimes, the process parameters and the equipment used to extrude the tubing are as important as or even more important than the actual dimensions of the tube.

The medical tubing (T) according to the present invention can be a single lumen tubing that is characterized by its dimensions.

The tubing length (L) of the medical tubing (T) is not particularly limited. It can differ broadly depending on the particularly encompassed application. Generally, it ranges from 1.0 mm to 10 m. The tubing length (L) may be of at least 2.0 mm, at least 5.0 mm, at least 10 mm, at least 20 mm, at least 50 mm, at least 10 cm, at least 20 cm, at least 50 cm, at least 1.0 m, at least 2.0 m or at least 5.0 m; besides, it may be of at most 5.0 m, at most 2.0 m, at most 1.0 m, at most 50 cm, at most 20 cm, at most 10 cm, at most 50 mm, at most 20 mm, at most 10 mm, at most 5.0 mm or at most 2.0 mm.

When the lumen has a circular cross-section, the tubing inner diameter (ID), the tubing outer diameter (OD) and the tubing wall thickness (WT).

The tubing inner diameter (ID) of the medical tubing (T) is advantageously below 1.9 cm. It may be below 1.6 cm, below 1.3 cm or even below 1.0 cm. The tubing inner diameter (ID) of the medical tubing (T) is sometimes much smaller and may reach values of at most 0.50 cm, at most 0.20 cm or at most 0.10 cm. The tubing inner diameter (ID) of the medical tubing (T) may even be of at most 0.60 mm, at most 0.40 mm, at most 0.30 mm, at most 0.20 mm or at most 0.15 mm. Besides, the tubing inner diameter (ID) of the medical tubing (T) may be of at least 0.05 mm, 0.10 mm, at least 0.20 mm, at least 0.50 mm, at least 0.10 cm, at least 0.20 cm, at least 0.50 cm or at least 1.0 cm.

The tubing outer diameter (OD) of the medical tubing (T) is advantageously below 2.8 cm. It may be below 2.2 cm, below 1.5 cm or even below 1.0 cm. The tubing outer diameter (OD) of the medical tubing (T) is sometimes much smaller and may reach values of at most 0.80 cm, at most 0.50 cm, at most 0.30 cm or at most 0.20 cm. The tubing outer diameter (OD) of the medical tubing (T) may even be below 0.10 cm, of at most 0.80 mm, at most 0.60 mm, at most 0.40 mm, at most 0.30 mm or at most 0.20 mm. Besides, the tubing outer diameter (OD) of the medical tubing (T) may be of at least 0.10 mm, at least 0.20 mm, at least 0.50 mm, at least 0.10 cm, at least 0.20 cm, at least 0.50 cm, at least 1.0 cm or at least 2.0 cm.

The tubing wall thickness (WT) of the medical tubing (T) is advantageously below 0.40 cm. It may be below 0.20 cm, below 0.15 cm or even below 0.10 cm. The tubing wall thickness (WT) of the medical tubing (T) is sometimes much smaller and may reach values of at most 0.080 cm, 0.050 cm or 0.020 cm. The tubing wall thickness (WT) of the medical tubing (T) may even be below 0.015 cm, of at most 0.10 mm or at most 0.080 mm. Besides, the tubing wall thickness (WT) of the medical tubing (T) according to the present invention may be of at least 0.020 mm, at least 0.050 mm, at least 0.10 mm, at least 0.20 mm, at least 0.50 mm, at least 0.10 cm or at least 0.20 cm.

For example, medical tubings (T) according to the present invention have the following dimensions: (i) a tubing inner diameter (ID) of 0.50 cm, a tubing outer diameter (OD) of 0.90 cm and a tubing wall thickness (WT) of 0.20 cm, (ii) a tubing inner diameter (ID) of 0.35 cm, a tubing outer diameter (OD) of 0.50 cm and a tubing wall thickness (WT) of 0.075 cm, (iii) a tubing inner diameter (ID) of 0.22 cm, a tubing outer diameter (OD) of 0.28 cm and a tubing wall thickness (WT) of 0.03 cm, (iv) a tubing inner diameter (ID) of 0.09 cm, a tubing outer diameter (OD) of 0.11 cm and a tubing wall thickness (WT) of 0.01 cm, and (v) a tubing inner diameter (ID) of 0.20 mm, a tubing outer diameter (OD) of 0.10 mm and a tubing wall thickness (WT) of 0.05 mm.

When the medical tubing (T) is a single lumen tubing with a non circular inner cross-section, such as a polygonal or elliptical inner cross-section, the inner diameter (ID) is calculated as the equivalent circular diameter, i.e. the diameter of the circle of equal area to that of the area of the inner cross-ssection. The wall thickness (WT) is then calculated as the difference between the outer diameter (OD) and the so-calculated inner diameter (ID).

The medical tubing (T) may consist of one part (the "single part"). Then, the single part consists of the polymer material (M).

Alternatively, the medical tubing (T) may consist of several parts. The case being, either one part or several parts of the medical tubing (T) may consist of the polymer material (M). When several parts of the medical tubing (T) consist of the polymer material (M), each of them may consist of the same polymer material (M); alternatively, at least two of them differ from each other by the chemical nature of the polymer material (M).

The medical tubing (T) in accordance with the present invention is especially useful for therapeutically or surgically treating a patient.

Examples of applications of the medical tubing (T) include high pressure catheter tubing; tubing used to make angioplasty and stent delivery catheters; balloon tubing used to fabricate medical balloons, especially high pressure angioplasty and stent delivery balloons; tubing that will be implanted or inserted in the body for long periods of time; and other Preferred medical tubings (T) are selected from the group of catheters and guidewires.

In a first preferred embodiment (E1), the medical tubing (T) is a medical device exactly as described in WO 2006/037078, except that the rigid-rod polyphenylene included in the medical device of WO 2006/037078 is completely replaced, weight pro weight, by the kinked rigid-rod polyphenylene (P) as above described. In particular, in accordance with embodiment (E1), the medical tubing (T) may be:

a medical device (T1) for therapeutically treating a patient by advancing along a body passage to a desired site for treatment, comprising a flexible polymer component made of the kinked rigid-rod polyphenylene (P), wherein the component has sufficient strength and flexibility that the component has no reinforcement;

the medical device (T1) as above described, which is a catheter, and the flexible polymer component is a catheter shaft defining a lumen;

the medical device (T1) as above described, which is a catheter, and the flexible polymer component is a catheter shaft defining a lumen, and the catheter further comprises a balloon affixed to a distal end of the catheter shaft, wherein the balloon is made of the kinked rigid-rod polyphenylene (P);

the medical device (T1) as above described, which is a guidewire;

the medical device (T1) as above described, which is selected among the group of: balloon catheters, diagnostic catheters, guiding catheters, stent delivery system catheters, injection catheters, gene therapy catheters, electrophysiology catheters, therapeutic drug delivery catheters, ultrasound catheters, and laser angioplasty catheters;

a balloon catheter (T2) comprising: a catheter shaft having a proximal and distal end, defining an inflation lumen; a polymer balloon affixed to the catheter shaft near the distal end, the inflation lumen communicating with an interior of the balloon; at least a portion of the balloon catheter being made of the kinked rigid-rod polyphenylene (P);

the balloon catheter (T2) as above described, wherein the balloon is made of the kinked rigid-rod polyphenylene (P);

the balloon catheter (T2) as above described, wherein at least a portion of the catheter shaft is formed of the kinked rigid-rod polyphenylene (P);

the balloon catheter (T2) as above described, wherein the balloon is an angioplasty balloon;

the balloon catheter (T2) as above described, further comprising a stent crimped around the balloon, such that inflation of the balloon will expand and deploy the stent;

a catheter (T3), comprising a tubular shaft member, at least a portion of the shaft member being made of the kinked rigid-rod polyphenylene (P);

the catheter (T3) as above described, at least a portion of the shaft member being made of a blend of the kinked rigid-rod polyphenylene (P) and another polymer.

An example of the medical tubing (T) is a catheter shaft. Stronger, thinner catheter shafts are desirable in various types of medical devices, including cardiovascular, endovascular and neurovascular catheter products. Self-reinforcing polymer shafts made of the kinked rigid-rod polyphenylene (P) provide superior shafts for these types of catheters.

The self-reinforcing nature of the kinked rigid-rod polyphenylene (P) allows for thinner wall extrusions without sacrificing strength or stiffness, which translates into catheter deliverability, pushability and steerability.

Catheters of the present invention are often intended to follow a specific path through body passages selected by a physician. They may be of many different kinds and types, including for example balloon catheters, diagnostic catheters, guiding catheters, stent delivery system catheters, injection catheters, gene therapy catheters, electrophysiology catheters, therapeutic drug delivery catheters, ultrasound catheters, laser angioplasty catheters, etc.

Structurally, catheters may have a flexible shaft extending between a proximal end and a distal end, and may define one or more tubular passages or "lumens" extending through part or all of the catheter shaft. Such lumens often have one or more openings, referred to as "ports," or a lumen may have a closed lumen.

When a lumen is adapted to slidingly receive a guidewire, it is referred to as a "guidewire lumen," and it will generally have a proximal and distal "guidewire port". The distal guidewire port is often at or near the catheter shaft distal end.

A hub is often affixed to the catheter shaft proximal end. The hub may serve a variety of functions, including providing a handle for manipulating the catheter, and/or defining proximal port(s) communicating with lumen(s) defined by the catheter shaft. When the catheter has a guidewire lumen, a proximal guidewire port may be located at some point along the sidewall of the catheter shaft, or a hub may define the proximal guidewire port.

Catheter balloons represent another possible example of this invention. Since the kinked rigid-rod polyphenylene (P) can be extruded into thin-wall tubes, biaxially orienting the tube into a high strength balloon is feasible. Since kinked rigid-rod polyphenylene boasts tensile strength of up to 30 ksi, balloons prepared from this material are very thin and strong. For example, balloons of the kinked rigid-rod polyphenylene (P) may have nominal inflation pressures well in excess of 25 atmospheres.

Examples of additional types of catheters made of the kinked rigid-rod polyphenylene (P) include stent delivery system catheters, injection catheters, gene therapy catheters, electrophysiology catheters, therapexitic drug delivery catheters, ultrasound catheters, laser angioplasty catheters, etc.

Other possible embodiments of this invention include guidewires, hypotubes, and marker bands. A guidewire has a flexible wire-like structure extending from a proximal end to a distal end. The guidewire will usually be of a size selected to fit into and slide within a corresponding guidewire lumen of a catheter.

Because the strength of the kinked rigid-rod polyphenylene (P) puts this property in the range of metals, and its ability to extrude, injection mold and solvent-cast, replacement of metal components in catheter systems is possible. This feature is particularly beneficial for MR (magnetic resonance) compatible catheter systems. In the case of marker bands, kinked rigid-rod polyphenylene can be doped with appropriate radioopaque material and then extruded to create marker bands with low profile.

It is of course possible to build various kinds and designs of medical tubings (T) according to the present invention, by various techniques and of various materials, to obtain the desired features.

FIG. 1 shows for example a diagnostic catheter or a guiding catheter having a flexible tubular shaft extending between proximal and distal ends, a hub affixed to the proximal end, and a strain relief positioned at trie transition. Again, any or all of the components of the diagnostic catheter shown in FIG. 1 may be made of the kinked rigid-rod polyphenylene (P).

In a second preferred embodiment (E2), the medical tubing (T) is a medical device, such as a guidewire or a catheter, exactly as described in WO 2005/102406, except that the thermoplastic rigid-rod polymer included in the medical device of WO 2005/102406 is completely replaced, weight pro weight, by the kinked rigid-rod polyphenylene (P) as above described. In particular, in accordance with embodiment (E2), the medical tubing (T) may be:

a guidewire (T4) comprising: an atraumatic distal tip; a proximal end; an elongate core made from the kinked rigid-rod polyphenylene (P), the core extending from the atraumatic distal tip to the proximal end; and a polymeric sheath disposed over the core;

the guidewire (T4) as above described, wherein the elongate core comprises a plurality of long, flexible elements disposed in parallel;

a medical device (T5) comprising an elongate flexible element made from a first polymer which is the kinked rigid-rod polyphenylene (P);

the medical device (T5) as above described, wherein it is an intravascular guidewire, the elongate flexible element being possibly a core wire, wherein the core wire comprises a plurality of elongate longitudinally extending thready made of the kinked rigid-rod polyphenylene (P);

the medical device (T5) as above described, wherein it is an intravascular guidewire, the elongate flexible element being a sleeve extending over the core wire and further comprising a second sleeve disposed on the first, the second sleeve made from the kinked rigid-rod polyphenylene (P);

the medical device (T5) as above described, wherein it is a catheter;

the medical device (T5) as above described, wherein it is a catheter, the flexible elongate member being a sleeve the medical device (T5) as above described, wherein it is a catheter, the flexible elongate member being a first sleeve, and the catheter further comprises a second sleeve disposed on the first, the second sleeve being made from the kinked rigid-rod polyphenylene (P).

the medical device (T5) as above described, wherein the elongate flexible element comprises a blend of the first polymer and a second polymer;

the medical device (T5) as above described, wherein the medical device comprises a second polymer, wherein the first polymer is not cross-linked and the second polymer is cross-linked;

the medical device (T5) as above described, wherein the medical device comprises a balloon, the elongate flexible element being a balloon sleeve;

the medical device (T5) as above described, wherein the medical device comprises a balloon, the elongate flexible element being a balloon sleeve, and the balloon sleeve comprising a second polymer, the first polymer and the second polymer being preferably coextruded, the first polymer being preferably not cross-linked and the second polymer being preferably cross-linked.

the medical device (T5) as above described, wherein the elongate member comprises a plurality of struts forming a stent, the stent preferably further comprising a hydrogel coating including a therapeutic agent;

the medical device (T5) as above described, wherein the elongate member comprises a paramagnetic material, such as gadolinium (III).

One example embodiment pertains to an elongated medical device comprising a flexible elongated element consisting of the polymer material (M) comprising the kinked rigid-rod polyphenylene (P). The element may provide a significant portion of the medical devices mechanical characteristics such as torqueability, pushability, and flexibility.

Another example embodiment pertains to a guidewire comprising a elongated member consisting of the polymer material (M) comprising the kinked rigid-rod polyphenylene (P). The elongated member may be a core wire-of the guidewire. The core wire may run from substantially the proximal portion of the guidewire to the distal portion of the guidewire. The core wire may have a generally circular cross-sectional shape or may have a rectangular or X-shaped cross-sectional shape. The guidewire may include a sheath made from the kinked rigid-rod polyphenylene (P) or may include more than one sheath made from the kinked rigid-rod polyphenylene (P). The sheath may be an extruded sleeve or may be a braided sleeve. The braid may be a diamond braid or may be a crisscross braid. The guidewire may include a core having a plurality of fine threads of the consisting of the polymer material (M) comprising the kinked rigid-rod polyphenylene (P) extending through a substantial length of the guidewire.

The guidewire may have a first section having a solid core consisting of the polymer material (M) comprising the kinked rigid-rod polyphenylene (P) and a second section having a plurality of fine threads consisting of the polymer material (M) comprising the kinked rigid-rod polyphenylene (P). The guidewire may have variable stiffness which may be provided by controlling the outer diameter of a polymer shaft.

Another example embodiment of the present invention pertains to a catheter such as a guide catheter.

The elongated member may be a sleeve consisting of the polymer material (M) comprising the kinked rigid-rod polyphenylene (P). The sleeve may include two or more layers consisting of the polymer material (M) comprising the kinked rigid-rod polyphenylene (P). The sleeve may be braided, either in a diamond pattern or a crisscross pattern. The braided layer may be coated with another polymer material and thereby impregnated with another polymer material. The sleeve may also be woven. The sleeve may be a coiled polymer ribbon or may be a spring. The polymer material (M) of the sleeve may be blended or co-extruded with another polymer material. The other polymer may be a thermoplastic. The blend or thickness of the layers of the coextrusion may vary along the length to provide different mechanical characteristics along desired portions.

Another example embodiment pertains to a balloon catheter such as an angioplasty or stent-delivery catheter having a balloon sleeve consisting of the polymer material (M) comprising the kinked rigid-rod polyphenylene (P). The balloon sleeve may have a first layer that is the polymer material (M) and a second layer that is another polymer material, such as a non-crosslinked nylon.

The balloon may have a wall formed using variable coextrusion, with this polymer used where certain characteristics such as non-compliance are desired and another polymer where other characteristics are desired. The balloon wall may be formed from a weave or mesh of this polymer coated with or overlaying another polymer.

Figure 2:
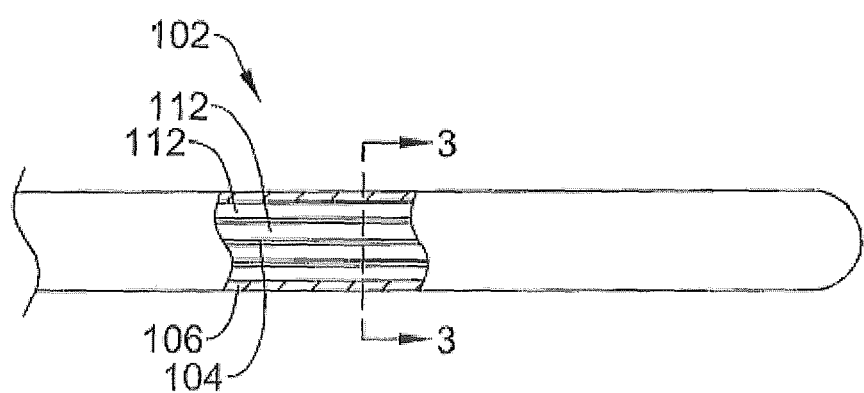
FIG. 2 depicts a diagrammatic cross sectional view of a guidewire in accordance with the present invention.

FIG. 2 is a diagrammatic cross sectional view of an example guidewire 102.

Guidewire 102 includes a core 104 formed from a plurality of elongate fibers 112, several of the fibers 112 consisting of the polymer material (M) comprising the kinked rigid-rod polyphenylene (P), and may include a lubricious or polymeric sheath 106. Of course, all fibers 112 may consist of the polymer material (M) comprising the kinked rigid-rod polyphenylene (P). Alternatively, some fibers 112 may consist of the polymer material (M) comprising the kinked rigid-rod polyphenylene (P) and other fibers 112 may include other polymer materials. Some fibers 112 may vary from a first material to a second material along the length of the fiber. Fibers 112 are selected to provide for desired characteristics along the length of guidewire 102. The number and composition of fibers 112 affect the performance of guidewire 102. Generally the more fibers that include a kinked rigid rod polymer, and the more of that material that is in each fiber, the fewer fibers are needed to achieve a desired level of torqueability and pushability.

Other variations are contemplated as well. For instance Fibers 112 may be of variable length to permit the guidewire to taper distally. Thus, all fibers 112 would be present at a proximal portion and fewer fibers would be present distally. Alternatively, each fiber may have a tapering cross section. Variations in the cross-sectional shape are contemplated. For instance, the cross-sectional shape of certain fibers may be circular, pentagonal or square. Changing the cross-sectional shape of the fibers may change the torqueability while keeping the flexibility substantially the same, for example. Fibers 112 are retained in a sheath 106 and may be bonded at distal and proximal locations. Select fibers may also be bonded to each other or to the sheath at various other locations throughout the guidewire, which may help impart a desired shape to the guidewire.

Any of the medical tubings (T) in accordance with the present invention and described herein may be provided with a coating on a surface of the tubings. Such coatings may be provided for various purposes including, but not limited to, carrying a therapeutic agent for localized delivery to a target area within the body; providing a lubricious surface to facilitate introduction of the medical tubing (T) into the patient during an interventional procedure; improving the biocompatibility of the medical device with the surrounding environment; or, for a combination of such or other purposes.

The terms torqueability, pushability and flexibility are herein defined as follows. Torqueability is the ability to transmit a rotational force from a proximal portion to a distal portion. Torqueability may be advantageous if a guidewire is shaped to conform to specific vasculature, and the guidewire needs to be specifically oriented to take full advantage of its shape. Pushability is the ability to transmit a longitudinal force from a proximal portion to a distal portion so that the longitudinal displacement of the distal portion is approximately the same as the longitudinal displacement of the proximal portion. In contrast, a device that does not exhibit a high degree of pushability would displace laterally near the proximal portion, creating bends or curves in the device. Flexibility is the ability of a device to bend without breaking or permanent deformation.

Medical tubings (T) as above described are typically sterilized and small in diameter. It appears that such tubings may find useful applications in many other fields than the medical field, in particular building and automotive applications.

Therefore, another aspect of the present invention is related to a tubing, in particular to a tubing different from a medical tubing (T), comprising at least one kinked rigid-rod polyarylene (P) of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix (M) consisting of:

between 0 and 75 mole %, based on the total number of moles of the recurring units (R), of rigid rod-forming arylene units (Ra), said rigid rod-forming arylene units (Ra) being optionally substituted by at least one monovalent substituting group, with between 25 and 100 mole %, based on the total number of moles of the recurring units (R), of kink-forming arylene units (Rb), said kink-forming arylene units (Rb) being optionally substituted by at least one monovalent substituting group.

wherein the tubing wall thickness (WT) is below 0.1 cm.

The tubing according to the present invention features preferably all the above described characteristics of the medical tubing (T).

The tubing inner diameter (ID) of the tubing according to the present invention is advantageously below 1.9 cm. It may be below 1.6 cm, below 1.3 cm or even below 1.0 cm. The tubing inner diameter (ID) of the tubing according to the present invention is sometimes much smaller and may reach values of at most 0.50 cm, 0.20 cm or 0.10 cm. The tubing inner diameter (ID) of the tubing according to the present invention may even be below 0.09 cm.

The tubing outer diameter (OD) of the tubing according to the present invention is advantageously below 2.8 cm. It may be below 2.0 cm, below 1.5 cm or even below 1.0 cm. The tubing outer diameter (OD) of the tubing according to the present invention is sometimes much smaller and may reach values of at most 0.80 cm, 0.50 cm or 0.20 cm. The tubing outer diameter (OD) of the tubing according to the present invention may even be below 0.10 cm.

The tubing wall thickness (WT) of the tubing according to the present invention is advantageously below 0.40 cm. It may be below 0.20 cm, below 0.15 cm or even below 0.10 cm. The tubing wall thickness (WT) of the tubing according to the present invention is sometimes much smaller and may reach values of at most 0.08 cm, 0.05 cm or 0.02 cm. The tubing wall thickness (WT) of the tubing according to the present invention may even be below 0.015 cm.

The tubing length (L) of the tubing according to the present invention is not particularly limited. It can differ broadly depending on the particularly encompassed application. Generally, it ranges from 1.0 mm to 10 m. The tubing length (L) of the tubing according to the present invention may be of at least 2.0 mm, at least 5.0 mm, at least 10 mm, at least 20 mm, at least 50 mm, at least 10 cm, at least 20 cm, at least 50 cm, at least 1.0 m, at least 2.0 m or at least 5.0 m; besides, it may be of at most 5.0 m, at most 2.0 m, at most 1.0 m, at most 50 cm, at most 20 cm, at most 10 cm, at most 50 mm, at most 20 mm, at most 10 mm, at most 5.0 mm or at most 2.0 mm.

The medical tubing (T) and other tubings of the present invention present lots of unexpected advantages.

They can meet a confluence of quite important characteristics for tubings:
they exhibit advantageously a high torqueability, in substantial progress when compared to the prior art tubings made of rigid-rod poly(1,4-phenylene);
they exhibit advantageously a high flexibility, also in substantial progress when compared to the prior art tubings made of rigid-rod poly(1,4-phenylene);
they exhibit advantageously a high pushability, a high deliverability and a high steerability, as may be needed e.g. by lots of medical tubings such as catheters, stents and guidewires, at least substantially as good as, and possibly better than, the prior art tubings made of rigid-rod poly(1,4-phenylene)
they can be easily thin-wall extruded under especially harsh conditions (e.g. by using an extruder with extremely small orifices).
they are advantageously non toxic and non irritant; they can even have all the attributes of a biocompatible material.

The medical tubing (T) and other tubings of the present invention exhibit further advantageously a high compression and flexural strength, a high rigidity, a high stiffness, a high surface hardness, a high ductility, a high impact resistance, a high chemical resistance, a high corrosion resistance, non combustibility, low moisture absorption.

The medical tubing (T) and other tubings of the present invention are advantageously easily disposable. They cannot just be easily disposed, they can further be recycled to form other shaped articles.

The Needle (N)

In a certain particular embodiment of the present invention of special interest, the medical tubing (T) and the tubing according to the present invention as above described are selected from the group of hollow needles.

Hence, this particular embodiment concerns a needle (N) comprising a body extending along a longitudinal axis and having two ends, wherein:
at least one end of the body is beveled, the body has a hollow section all along its longitudinal axis, and the body comprises the polymer material (M) comprising the at least one kinked rigid-rod polyarylene (P), namely a kinked rigid-rod polyarylene of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix (M) consisting of:

between 0 and 75 mole %, based on the total number of moles of the recurring units (R), of rigid rod-forming arylene units (Ra), said rigid rod-forming arylene units (Ra) being optionally substituted by at least one monovalent substituting group, with between 25 and 100 mole %, based on the total number of moles of the recurring units (R), of kink-forming arylene units (Rb), said kink-forming arylene units (Rb) being optionally substituted by at least one monovalent substituting group.

The needle (N) is typically a sharp pointed, slender instrument.

The needle (N) of the present invention is of particular interest when it is designed (and possibly, used) for the prevention, cure, alleviation, or correction of diseases, injuries, irregularities, disorders and deformities of any part of a human or animal body. The needle can be designed for use (and possibly, used) in non operative procedures (e.g. within the frame of a medical or dental therapy) or in operative procedures (e.g. within the surgical operation).

In certain preferred sub-embodiments, the needle (N) is a medical needle. For the purpose of the present invention, a "medical needle" is intended to denote a hollow needle designed to (and possibly, used to) introduce a material into or remove a material from a human or animal body, in general parenterally (e.g. intravenously, intramuscularily, or subcutaneously). The medical needle is commonly designed to be used (and is commonly used) attached to a syringe; the material can be injected or aspired.

In certain very preferred sub-embodiments, the needle (N) is a hypodermic needle. A hypodermic needle is a medical needle designed (and possibly, used) to introduce or remove from a human or animal body a material subcutaneously. It can be designed (and possibly, be used) to inject a liquid into the body. It can also be designed (and possibly, used) to take liquid samples from the body, for example taking blood from a vein in venipuncture. Large bore hypodermic intervention using a suitably designed hypodermic needle is especially useful in catastrophic blood loss or shock. A suitably designed hypodermic needle can also be used for rapid delivery of liquids, or when the injected substance cannot be ingested, either because it would not be absorbed (as with insulin), or because it would harm the liver. There are many possible routes for an injection, and it is further understood that the medical needle as herein broadly defined can be useful not only in non operative procedures, but also in operative ones. Hypodermic needles are usually used by medical professionals (physicians, nurses, paramedics), but they are sometimes used by patients themselves; this is common notably with certain diabetics who may require several insulin injections a day.

In certain other very preferred sub-embodiments, the material is a vaccin to be injected parenterally into a human or animal body.

In other preferred sub-embodiments, the needle (N) is a reconstitution needle. A reconstitution needle is designed (and possibly used) to penetrate a first sealed vial containing a first material through its seal (e.g. rubber stopper or other cap), then drawing up the first material into a syringe for mixing or injecting into a second sealed vial, etc. The reconstitution needle is particularly useful for medical applications, e.g. for mixing drugs or for diluting concentrated or lyophilized drugs in a diluent; once a desired drug is finally obtained, the reconstitution needle is removed from the syringe, and a traditional hypodermic needle is then generally used for injecting the final material into the body of a human or animal patient. The reconstitution needle is also useful for cosmetic applications like for reconstituting a neurotoxin solution, e.g. for drawing up in a syringe a proper amount of a saline contained in a first vial then inserting and injecting this amount of saline in a second vial containing a vacuum-dried neurotoxin such as onabotulinumtoxin A; then, the reconstitution needle is removed from the syringe, and a traditional hypodermic needle is then generally used for the injection the neurotoxin-contg. solution into the muscles of a human.

In still other sub-embodiments, the needle (N) is a cosmetic needle. For the purpose of the present invention, a cosmetic needle is intended to denote a needle designed for (and possibly, used in) a treatment tending to beautify, to preserve, restore or confer comeliness, to improve the appearance of a physical feature, irregularity or defect of a human or animal body. A cosmetic needle can be useful for injecting collagen.

Usually, the needle (N) consists essentially of, or even consists of the body extending along a longitudinal axis and having two ends. The body extending along a longitudinal axis and having two ends of the needle (N) can represent more than 50 wt. %, more than 75 wt. %, more than 90 wt. %, more than 95 wt. %, more than 99 wt. %, up to 100 wt. % of the total weight of the needle (N). Unless otherwise specified, whenever the terms "the body of the needle (N)" are used within the present specification, they are intended to designate the body extending along a longitudinal axis and having two ends, which is the only essential body of the presently invented needle.

The body of the needle (N) is advantageously essentially cylindrical. Preferably, it is cylindrical.

The body of the needle (N) can be extended along a straight, curving or bent, continuous or discontinuous, longitudinal axis. The body of the needle (N) is preferably extended along a straight, continuous longitudinal axis.

The body of the needle (N) has a hollow section all along its longitudinal axis. The hollow section of the body allows typically for the transportation of material, typically a liquid. The hollow section of the body is not particularly limited in shape; it can be polygonal, essentially elliptic or essentially circular; preferably, it is circular.

Figure 3:
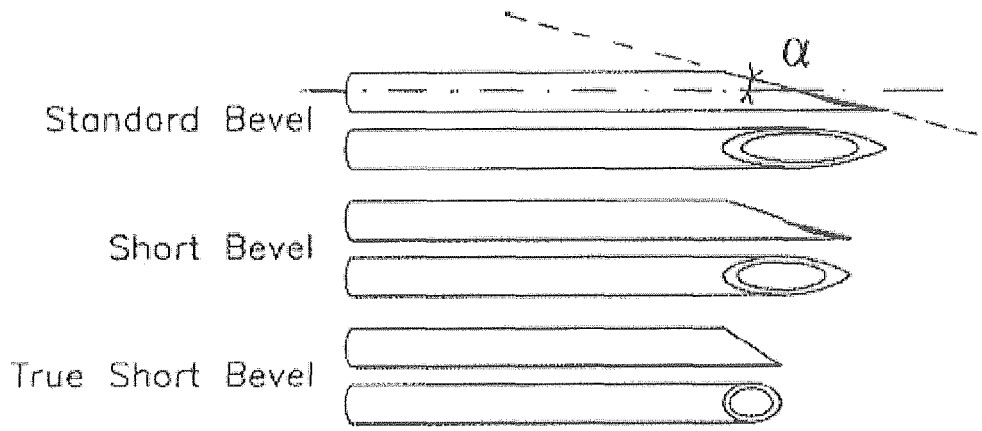
FIG. 3 depicts standard, short and true short bevels suitable for terminating the body of hypodermic needles in accordance with the present invention.

The body of the needle (N) has two ends. In certain preferred sub-embodiments, the body of the needle (N) is beveled at one and only one end. In other sub-embodiments of the invention, as will be detailed hereinafter, the body is beveled at both ends. The shape of the beveled end(s) [or bevel(s)] is not particularly limited; examples of certain standard, short and true short bevels suitable for terminating the body of the needle (N), such as a hypodermic needle, are illustrated in FIG. 3. The acuteness of the bevel can be related to the angle α which the longitudinal axis of the body makes with the bevel (more precisely, with the plane incorporating the oblique surface of the bevel). α ranges generally from 2.5° to 60°. α may be of at most 45°, at most 35°, at most 25°, at most 20° or at most 15°. Besides, α may be of at least 3.0°, at least 4.0°, at least 5.0°, at least 6.0°, at least 7.0°, at least 8.0°, at least 9.0°, at least 10°, at least 12°, at least 15°, at least 20°, at least 25° or at least 30°. In particular, the bevel terminating the body of the needle (N) can be a standard bevel, substantially as shown on FIG. 3; it can be a short bevel, substantially as shown on FIG. 3; it can also be a true short bevel, substantially as shown on FIG. 3.

In certain preferred sub-embodiments, the body of the needle (N) is essentially composed of, or is even composed of, the polymer material (M). Very preferably, the needle (N) is essentially composed of, or is even composed of, the polymer material (M).

In other preferred sub-embodiments, the needle is essentially free, or is even free, of reinforcement filaments embedded in the polymer material (M), such as stainless steel reinforcement filaments. In other preferred sub-embodiments of the invention, the needle is essentially free, or is even free, of any metal or metal alloy.

Good results are obtained notably when the needle (N) consists essentially of the body, said body being essentially cylindrical, said body having an essentially circular hollow section, said body being beveled at one and only one end, and said body being essentially composed of the polymer material (M). Good results are also obtained when the needle (N) consists of the body, said body being cylindrical, said body having a circular hollow section all along its longitudinal axis, said body being beveled at one and only one end, and said body being composed of the polymer material (M).

In certain non preferred sub-embodiments, the body of the needle (N) is a "composite body". Typically, a composite body comprises at least one structural part in addition to the polymer material (M), separated therefrom but connected thereto. The additional structural part can be in the form of filaments, such as stainless steel reinforcement filaments. A particular needle (N) in accordance with the present invention comprises a body extending along a longitudinal axis and having two ends, wherein the body consists essentially (or even, consists) of the polymer material (M) and of stainless steel reinforcement filaments embedded in the polymer material (M) and extending parallel to the longitudinal axis.

The needle (N) can be characterized by its length (L), its outer diameter (OD), its inner diameter (ID) and its wall thickness (WT).

The length of the needle (N) is generally of at most 300 mm, very often of at most 200 mm, often of at most 100 mm. It may be of at most 70 mm, at most 40 mm, at most 30 mm, at most 20 mm, at most 15 mm, at most 10 mm or at most 5.0 mm. Besides, the length of the needle (N) is generally of at least 1.0 mm, very often of at least 2.0 mm, often of at least 3.0 mm. It may be of at least 5.0 mm, at least 10 mm, at least 15 mm, at least 20 mm, at least 30 mm, at least 40 mm or at least 70 mm.

The outer diameter (OD) of the needle (N) is generally of at most 20 mm, very often of at most 10 mm, often of at most 5.0 mm. It may be of at most 4.0 mm, at most 3.0 mm, at most 2.0 mm, at most 1.5 mm, at most 1.0 mm, at most 0.80 mm, at most 0.60 mm, at most 0.40 mm, at most 0.30 mm or at most 0.20 mm. Besides, the outer diameter (OD) of the needle (N) is generally of at least 0.05 mm, very often of at least 0.10 mm, often of at least 0.15 mm. It may be of at least 0.20 mm, at least 0.30 mm, at least 0.40 mm, at least 0.60 mm, at least 0.80 mm, at least 1.0 mm, at least 1.5 mm, at least 2.0 mm or at least 3.0 mm.

The inner diameter (ID) of the needle (N) is generally of at most 12 mm, very often of at most 8.0 mm, often of at most 4.0 mm. It may be of at most 3.0 mm, at most 2.0 mm, at most 1.5 mm, at most 1.0 mm, at most 0.80 mm, at most 0.60 mm, at most 0.40 mm, at most 0.30 mm, at most 0.20 mm or at most 0.15 mm. Besides, the inner diameter (OD) of the needle (N) is generally of at least 0.015 mm, very often of at least 0.030 mm, often of at least 0.060 mm. It may be of at least 0.080 mm, at least 0.15 mm, at least 0.20 mm, at least 0.25 mm, at least 0.30 mm, at least 0.40 mm, at least 0.60 mm, at least 0.80 mm, at least 1.0 mm, at least 1.5 mm, at least 2.0 mm or at least 3.0 mm.

The wall thickness (WT) of the needle (N) is generally of at most 5.0 mm, very often of at most 2.5 mm, often of at most 0.50 mm. It may be of at most 0.40 mm, at most 0.30 mm, at most 0.20 mm, at most 0.15 mm, at most 0.10 mm or at most 0.080 mm. Besides, the wall thickness (WT) of the needle (N) is generally of at least 0.01 mm, very often of at least 0.02 mm, often of at least 0.03 mm. It may be of at least 0.040 mm, at least 0.060 mm at least 0.080 mm, at least 0.10 mm, at least 0.15 mm, at least 0.20 mm or at least 0.30 mm.

When the needle (N) is cylindrical, the outer diameter (OD) is calculated as the equivalent circular diameter, i.e. the diameter of the circle of equal area to that of the area of the outer cross-section. When the needle (N) has a non circular hollow cross-section, the inner diameter (ID) is calculated as the equivalent circular diameter, i.e. the diameter of the circle of equal area to that of the area of the inner cross-section. When the walls of the needle (N) do not form a circular crown, the wall thickness (WT) is calculated as the equivalent circular crown diameter.

The diameter of a medical needle, especially a hypodermic needle, is typically indicated by the needle gauge. Various needle lengths are generally available for a given gauge. There are a number of systems for gauging needles, including the Stubs Needle Gauge and the French Catheter Scale. Needles in common medical use range from 7 gauge (the largest) to 33 (the smallest) on the Stubs scale. Twenty-one-gauge needles are most commonly used for drawing blood for testing purposes, and sixteen- or seventeen-gauge needles are most commonly used for blood donation, as they are large enough to allow red blood cells to pass through the needle without rupturing (this also allows more blood to be collected in a shorter time). Larger-gauge needles (with smaller diameter) will rupture the red blood cells, and if this occurs, the blood is useless for the patient receiving it.

The needle (N) is advantageously sterile and apyrogenic. For this purpose, it is profitably manufactured, then packed in an original pack under sterile and apyrogenic conditions. It is preferably kept sterile and apyrogenic in the original pack until it is used, and it is further preferably used one and only one time.

Figure 4:
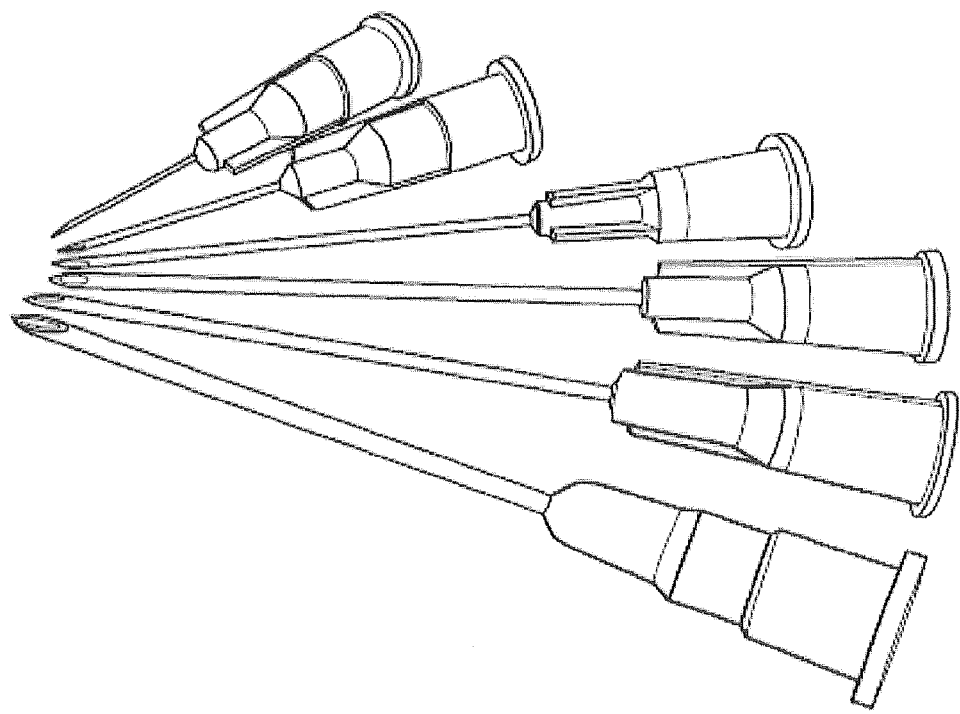
FIG. 4 depicts a hollow needle in accordance with the present invention needle which is embedded in a hub to be attached to the barrel of a syringe, typically by means of a press-fit or twist-on fitting ("Luer Lock" connection).

The needle (N) is advantageously a disposable needle. The needle (N), especially when it is disposable, is commonly embedded in a hub that is attached to the barrel of a syringe, typically by means of a press-fit or twist-on fitting, and is then commonly referred to as a "Luer Lock" connection, as shown in FIG. 4.

The hub can be composed of aluminum, of a plastic material other than the polymer material (M) such as a polyetheretherketone or a wholly aromatic polyester; preferably, the hub is essentially free or is free of metal; very preferably, the hub is composed of a polymer material (M') comprising at least one kinked rigid-rod polyarylene (P), said polymer material (M') being identical to or different from the polymer material (M).

Hence, another aspect of the present invention is directed to a hub capable of being attached to the barrel of a syringe, wherein the needle (N) is embedded in the hub and the hub comprises or is composed of the polymer material (M) (M') as previously defined. Related aspects of the invention are directed (i) to a needle system comprising a hub capable of being attached to the barrel of a syringe and of the needle (N) embedded in said hub, wherein the hub comprises or consists of the polymer material (M') as previously defined, and (ii) to a needle system consisting of a hub capable of being attached to the barrel of a syringe and of the needle (N) embedded in said hub, wherein the hub comprises or consists of the polymer material (M') as previously defined.

Still another aspect of the present invention is directed to a draining or administering cannula-based system comprising a cannula having a lumen and a trocar positioned in the lumen at one extremity of the cannula, wherein the trocar is the needle (N) as above described. A cannula is a usually flexible tube, designed to be inserted into a bodily cavity, duct, or vessel to drain fluid or administer a substance such as a medication, while a trocar is a sharp-pointed surgical instrument, designed to be used with a cannula to puncture a body cavity, duct or vessel for fluid aspiration. Preferably, the cannula is composed of a polymer material (M") comprising at least one kinked rigid-rod polyarylene (P), said polymer material (M") being identical to or different from the polymer material (M).

Still another aspect of the present invention is directed to an injection syringe comprising a piston, a pump body equipped with an end fitting for fitting of an injection needle, and an injection needle, wherein the injection needle is the needle (N) as above described. The body of the injection needle has generally a hollow section all along its longitudinal axis. Preferably, the pump body equipped with its end-fitting and the piston are composed of a polymer material (M''') comprising at least one kinked rigid-rod polyarylene (P), said polymer material (M''') being identical to or different from the polymer material (M).

Still another aspect of the present invention is directed to a recipient connector comprising a first hollow section suitable for fitting around neck of a first recipient, a second hollow section suitable for fitting around neck of a second recipient, the first hollow section and the second hollow section being separated from each other by a horizontal wall and a means of perforation of elastic capsules of the first and second recipients, wherein the means of perforation is the needle as above described, which is located at the center of the horizontal wall and the body of which is beveled at both ends.

It is of course possible to build various kinds and designs for the needle (N) according to the present invention, depending on the particularly encompassed end use.

The needle (N) can be manufactured using commonly known techniques to the skilled in the art for melt processing the polymer materials (M), (M'), (M") and (M'''), including extrusion, injection molding, compression molding and solution casting. The needle (N) can be notably manufactured using any method, or any step of a method described in any of the documents that have herein incorporated by reference. Reference can also be made to the "PrimoSpire® PR-250 SRP Injection Molding Guidelines" and to the "PrimoSpire® Self-Reinforced Polyphenylene (SRP) Machining Guidelines" brochures, made available by SOLVAY ADVANCED POLYMERS, L.L.C., the whole content of which is also herein incorporated by reference.

Hence, another aspect of the present invention is directed to a method of manufacturing the needle (N), which comprises melt processing, e.g. extruding, the polymer material (M).

Still another aspect of the present invention relates to the use of the needle (N) for any of the above described uses for which it has been designed, or to the use of the needle (N) in a medical, surgical or cosmetic application; the so-used needle is advantageously sterile and apyrogenic. In particular, the present invention relates to the use of the needle (N) for therapeutically or surgically treating a human or animal patient. This includes, for example, the use of the needle (N) as hypodermic needle, i.e. to introduce or remove a material subcutaneously from a human or animal body.

Still another aspect of the present invention relates to the disposal, e.g. by incineration, of the needle (N) after it has been used one and only one time.

Still another aspect of the present invention relates to a process for recycling the needle (N) as above described or the needle (N) used in accordance with any of the above described uses, which comprises:

(i) contacting the needle (N) with a solvent of the kinked rigid-rod polyarylene (P) so as to dissolve at least the kinked rigid-rod polyarylene (P) in the solvent;

(ii) causing at least the dissolved kinked rigid-rod polyarylene (P) to precipitate from the solvent e.g. by the addition of an anti-solvent; then (iii) recovering the precipitated kinked rigid-rod polyarylene (P) or a polymer material comprising the precipitated kinked rigid-rod polyarylene (P) e.g. in the form of powder or granules.

Examples of solvents of the kinked rigid-rod polyarylene (P) suitable for use in the present recycling process are described notably in the present specification, and include e.g. N-methylpyrrolidinone. Examples of anti-solvents of the kinked rigid-rod polyarylene (P) suitable for use in the present recycling process are also described in the present specification, and include e.g. isopropanol.

The recycling process may further comprise the step, subsequent to step (iii), of (iv) manufacturing a shaped article from the recovered kinked rigid-rod polyarylene (P) or from a polymer material comprising the precipitated kinked rigid-rod polyarylene (P).

Obviously, the present recycling process is also useful, and can thus also be used, for recycling any shaped article other than the needle (N), provided the shaped article of concern comprises a polymer material (M) comprising a kinked rigid-rod polyarylene (P), as the needle (N) does; among such other articles which can be recycled, it can be notably cited the medical tubing (T) or the tubing in accordance with the present invention as above described.

The needle (N) of the present invention presents lots of unexpected advantages.

It meets advantageously a confluence of characteristics including high compression and flexural strength, high rigidity, high stiffness, high surface hardness, high ductility, high impact resistance, high chemical resistance, high corrosion resistance, non combustibility, low moisture absorption.

The needle (N) has advantageously not just a good, but an excellent penetrability.

The needle (N) excels advantageously in its ability to hold a sharp edge. It can even be able to hold an extremely sharp edge.

The needle (N) is advantageously non toxic, non irritant. The needle (N) can even have all the attributes of a biocompatible material.

The needle (N) is advantageously easily disposable needles, hence especially well suited for a single-use. The needle (N) cannot just be easily disposed, it can further be recycled to form other shaped articles.

The needle (N) is advantageously made of a thermally stable material, and can be easily obtained by conventional melt processing techniques.

The Polymer Material (M)

The terms "polymer material" should be undertsood under their common meaning, i.e. a material containing polymer.

The polymer material (M) comprises at least one kinked rigid-rod polyarylene (P) as herein described, and can thus also be qualified as a "polyarylene material" or "kinked rigid-rod polyarylene material".

The polymer material (M) denotes indifferently a single kinked rigid-rod polyarylene (P), a polyarylene blend consisting of two or more kinked rigid-rod polyarylenes (P), or a polymer composition comprising at least one kinked rigid-rod polyarylene (P) and at least one other polymeric or non polymeric ingredient other than the kinked rigid-rod polyarylene (P).

The polymer material (M) can comprise one and only one kinked rigid-rod polyarylene (P). Alternatively, it can comprise two, three, or even more than three polyarylenes (P).

The Kinked Rigid-Rod Polyarylene (P)

For the purpose of the present invention, an arylene group is a hydrocarbon divalent group consisting of one core composed of one benzenic ring or of a plurality of benzenic rings fused together by sharing two or more neighboring ring carbon atoms, and of two ends.

Non limitative examples of arylene groups are phenylenes, naphthylenes, anthrylenes, phenanthrylenes, tetracenylenes, triphenylylenes, pyrenylenes, and perylenylenes. The arylene groups (especially the numbering of the ring carbon atoms) were named in accordance with the recommendations of the CRC Handbook of Chemistry and Physics, 64$^{th}$ edition, pages C1-C44, especially p. C11-C12.

Arylene groups present usually a certain level of aromaticity; for this reason, they are often reported as "aromatic" groups. The level of aromaticity of the arylene groups depends on the nature of the arylene group; as thoroughly explained in Chem. Rev. 2003, 103, 3449-3605, "Aromaticity of Polycyclic Conjugated Hydrocarbons", the level of aromaticity of a polycyclic aromatic hydrocarbon can be notably quantified by the "index of benzene character" B, as defined on p. 3531 of the same paper; values of B for a large set of polycyclic aromatic hydrocarbon are reported on table 40, same page.

An end of an arylene group is a free electron of a carbon atom contained in a (or the) benzenic ring of the arylene group, wherein an hydrogen atom linked to said carbon atom has been removed. Each end of an arylene group is capable of forming a linkage with another chemical group. An end of an arylene group, or more precisely the linkage capable of being formed by said end, can be characterized by a direction and by a sense; to the purpose of the present invention, the sense of the end of an arylene group is defined as going from the inside of the core of the arylene group to the outside of said core. As concerns more precisely arylene groups the ends of which have the same direction, such ends can be either of the same or opposite sense; also, their ends can be in the straight foregoing of each other, or not (otherwise said, they can be disjoint).

A polyarylene is intended to denote a polymer of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage. That the optionally substituted arylene group is linked by each of its two ends to two other optionally substituted arylene groups via a direct C—C linkage, is an essential feature of the recurring units (R); thus, an arylene recurring unit which is linked by at least one of its two ends to a group other than an arylene group such as phenylene recurring units $\phi_1$, $\phi_2$ and $\phi_2$, below:

—O-$\phi_1$-S(=O)$_2$—,

—O-$\phi_2\phi_2'$-O— are not recurring units (R) in the sense of the present invention.

The arylene groups of which the recurring units (R) consist can be unsubstituted. Alternatively, they can be substituted by at least one monovalent substituting group.

The monovalent substituting group is usually not polymeric in nature; its molecular weight is preferably below 500, more preferably below 300, still more preferably below 200 and most preferably below 150.

The monovalent substituting group is advantageously a solubilizing group. A solubilizing group is one increasing the solubility of the polyarylene in at least one organic solvent, in particular in at least one of dimethylformamide, N-methylpyrrolidinone, hexamethylphosphoric triamide, benzene, tetrahydrofuran and dimethoxyethane, which can be used as solvents during the synthesis of the polyarylene by a solution polymerization process.

The monovalent substituting group is also advantageously a group which increases the fusibility of the polyarylene, i.e. it lowers its glass transition temperature and its melt viscosity, so as to desirably make the polyarylene suitable for thermoprocessing.

Preferably, the monovalent substituting group is chosen from:

hydrocarbyls such as alkyls, aryls, alkylaryls and aralkyls;
halogens such as —Cl, —Br, —F and —I;
hydrocarbyl groups partially or completely substituted by at least one halogen atom such as halogenoalkyls, halogenoaryls, halogenoalkylaryls and halogenoaralkyls;
hydroxyl;
hydrocarbyl groups substituted by at least one hydroxyl group, such as hydroxyalkyls, hydroxyaryls, hydroxyalkylaryls and hydroxyaralkyls;
hydrocarbyloxys [—O—R, where R is a hydrocarbyl group], such as alkoxys, aryloxys, alkylaryloxys and aralkyloxys;
amino (—NH$_2$);
hydrocarbyl groups substituted by at least one amino group, such as aminoalkyls and aminoaryls;
hydrocarbylamines [—NHR or —NR$_2$, where R is a hydrocarbyl group] such as alkylamines and arylamines;
carboxylic acids and their metal or ammonium salts, carboxylic acid halides, carboxylic anhydrides;
hydrocarbyl groups substituted by at least one of carboxylic acids, metals or ammonium salts thereof, carboxylic acid halides and carboxylic anhydrides, such as —R—C(=O)OH where R is an alkyl or an aryl group;
hydrocarbylesters [—C(=O)OR or —O—C(=O)R, where R is a hydrocarbyl group] such as alkylesters, arylesters, alkylarylesters and aralkylesters;
amido [—C(=O)NH$_2$];
hydrocarbyl groups substituted by at least one amido group;
hydrocarbylamide monoesters [—C(=O)NHR or —NH—C(=O)—R, where R is a hydrocarbyl group], such as alkylamides, arylamides, alkylarylamides and aralkylamides, and hydrocarbylamide diesters [—C(=O)NR$_2$ or —N—C(=O)R$_2$, where R are a hydrocarbyl groups], such as dialkylamides and diarylamides;
sulfinic acid (—SO$_2$H), sulfonic acid (—SO$_3$H), their metal or ammonium salts,
hydrocarbylsulfones [—S(=O)$_2$—R, where R is the hydrocarbyl group], such as alkylsulfones, arylsulfones, alkylarylsulfones, aralkylsulfones;

aldehyde [—C(=O)H] and haloformyls [—C(=O)X, wherein X is a halogen atom];

hydrocarbylketones [—C(=O)—R, where R is a hydrocarbyl group], such as alkylketones, arylketones, alkylarylketones and aralkylketones;

hydrocarbyloxyhydrocarbylketones [—C(=O)—$R^1$—O—$R^2$, where $R^1$ is a divalent hydrocarbon group such as an alkylene, an arylene, an alkylarylene or an aralkylene, preferably a $C_1$-$C_{18}$alkylene, a phenylene, a phenylene group substituted by at least one alkyl group, or an alkylene group substituted by at least one phenyl group; and $R^2$ is a hydrocarbyl group, such as an alkyl, aryl, alkylaryl or aralkyl group], such as alkyloxyalkylketones, alkyloxyarylketones, alkyloxyalkylarylketones, alkyloxyaralkylketones, aryloxyalkylketones, aryloxyarylketones, aryloxyalkylarylketones and aryloxyaralkylketones;

any of the above groups comprising at least one hydrocarbyl group or a divalent hydrocarbon group $R^1$, wherein said hydrocarbyl group or said $R^1$ is itself substituted by at least one of the above listed monovalent substituting groups, e.g. an arylketone —C(=O)—R, where R is an aryl group substituted by one hydroxyl group;

where:
the hydrocarbyl groups contain preferably from 1 and 30 carbon atoms, more preferably from 1 to 12 carbon atoms and still more preferably from 1 to 6 carbon atoms;

the alkyl groups contain preferably from 1 to 18 carbon atoms, and more preferably from 1 to 6 carbon atoms; very preferably, they are chosen from methyl, ethyl, n-propyl, isopropyl, n-butyl, isobutyl and tert-butyl;

the aryl groups are defined as monovalent groups consisting of one end and one core composed of one benzenic ring (such the phenyl group) or of a plurality of benzenic rings directly linked to each other via a carbon-carbon linkage (such as the biphenyl group) or fused together by sharing two or more neighboring ring carbon atoms (such as the naphthyl groups), and wherein the ring carbon atoms are possibly substituted by at least one nitrogen, oxygen or sulfur atom; preferably, in the aryl groups, no ring carbon atom is substituted;

the aryl groups contain preferably from 6 to 30 carbon atoms; more preferably, they are phenyl groups;

the alkyl group which is contained in the alkylaryl groups meets the preferences of the alkyl groups as above expressed;

the aryl group which is contained in the aralkyl groups meets the preferences of the aryl groups as above expressed.

More preferably, the monovalent substituting group is chosen from hydrocarbylketones [—C(=O)—R, where R is a hydrocarbyl group] and hydrocarbyloxyhydrocarbylketones [—C(=O)—$R^1$—O—$R^2$, where $R^1$ is a divalent hydrocarbon group and $R^2$ is a hydrocarbyl group], said hydrocarbylketones and hydrocarbyloxyhydrocarbylketones being unsubstituted or substituted by at least one of the above listed monovalent substituting groups.

Still more preferably, the monovalent substituting group is chosen from arylketones and aryloxyarylketones, said arylketones and aryloxyarylketones being unsubstituted or substituted by at least one of the above listed monovalent substituting groups.

Most preferably, the monovalent substituting group is an (unsubstituted) arylketone, in particular it is phenylketone [—C(=O)-phenyl].

The core of the optionally substituted arylene group of the recurring units (R) is composed of preferably at most 3, more preferably at most 2, and still more preferably at most one benzenic ring. Then, when the core of the optionally substituted arylene group of the recurring units (R) is composed of one benzenic ring, the recurring units (R) are of one or more formulae consisting of an optionally substituted phenylene group, provided said optionally substituted phenylene group is linked by each of its two ends to two other optionally substituted arylene groups via a direct C—C linkage.

As above explained, the optionally substituted arylene group of the recurring units (R) is linked by each of its two ends to two other optionally substituted arylene groups via a direct C—C linkage. Preferably, it is linked by each of its two ends to two other optionally substituted phenylene groups via a direct C—C linkage.

As also above explained, both ends of the optionally substituted arylene group of the recurring units (R) can be characterized notably by a direction and by a sense.

A first set of recurring units (R) is composed of optionally substituted arylene groups, the ends of which
have the same direction,
are of opposite sense, and
are in the straight foregoing of each other
[hereafter, rigid rod-forming arylene units (Ra)].

Non limitative examples of such optionally substituted arylene groups include:

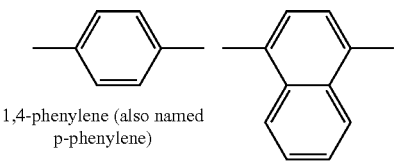

1,4-phenylene (also named p-phenylene)

1,4-naphthylene

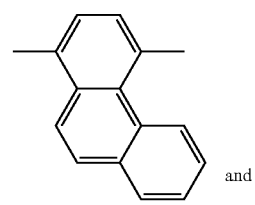

and

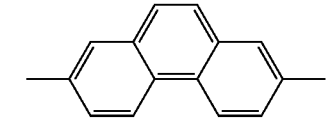

1,4-phenanthrylene and 2,7-phenanthrylene

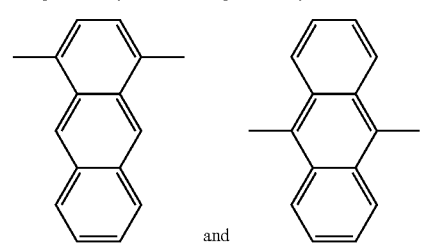

and 1,4-anthrylene and 9,10-anthrylene

-continued
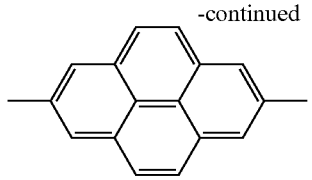
2,7-pyrenylene
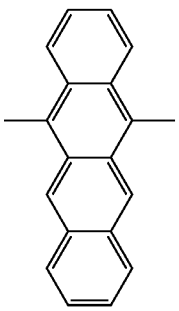
and
1,4-naphthacenylene and
5,12-naphthacenylene
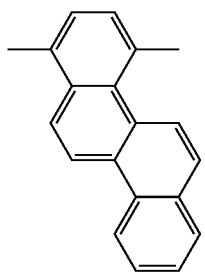
1,4-chrysenylene
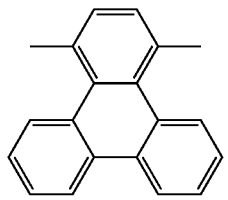
and
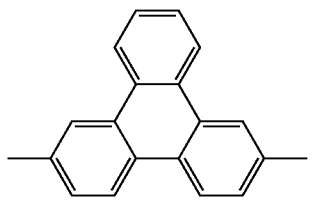
1,4-triphenylylene and
2,7-triphenylylene
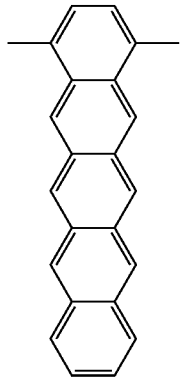
, and
-continued
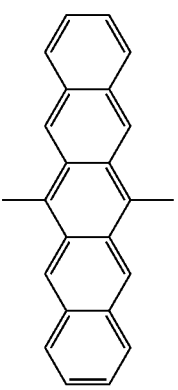
1,4-pentacenylene,
5,14-pentacenylene and
6,13-pentacenylene
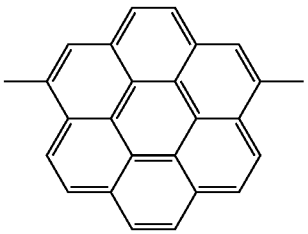
1,6-coronenylene
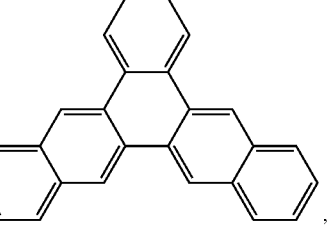
,
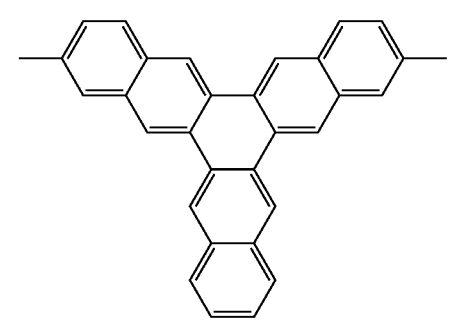
and

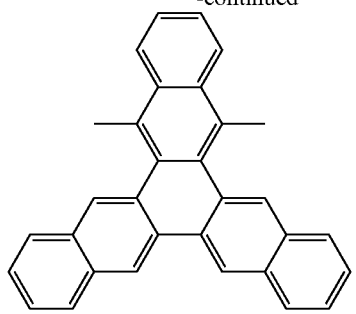

1,4-trinaphthylenylene,
2,9-trinaphthylenylene and
5,18-trinaphthylenylene and any of these groups substituted by at least one monovalent substituting group, as above defined, in particular by a phenylketone group.

Optionally substituted p-phenylenes are preferred as rigid rod-forming arylene units (Ra).

Rigid rod-forming arylene units (Ra), when contained in the polyarylenes, result in straight polymer chains exhibiting an outstanding rigidity. For this reason, such polyarylenes are commonly referred to as "rigid-rod polymers".

A second set of recurring units (R) is composed of optionally substituted arylene groups, the ends of which

- either have a different direction, forming thus together an angle between 0 and 180°, said angle being possibly acute or obtuse,
- or have the same direction and the same sense,
- or have the same direction, are of opposite sense and are disjoint (i.e. not in the straight foregoing of each other)

[globally hereafter referred to as kink-forming arylene units (Rb)].

Then, a first subset of kink-forming arylene units (Rb) is composed of optionally substituted arylene groups, the ends of which have a different direction, forming together an acute angle [kink-forming arylene units (Rb-1)]. Non limitative examples of optionally substituted arylene groups the ends of which have a direction different from each other include:

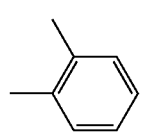

1,2-phenylene(or o-phenylene)

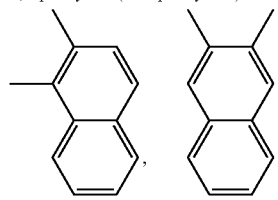 and 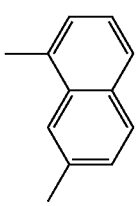

1,2-, 2,3- and 1,7-naphtylenes

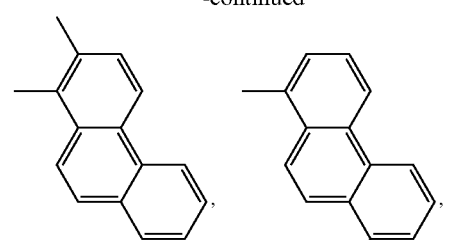

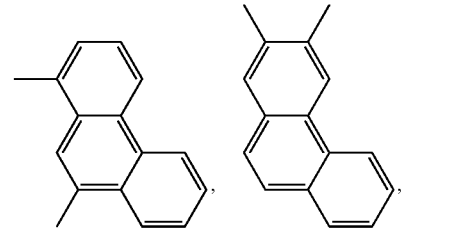

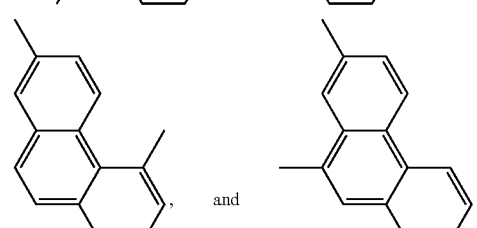

1,2-, 1,8-, 1,9-, 2,3-, 2,5- and 2,10-phenanthrylenes

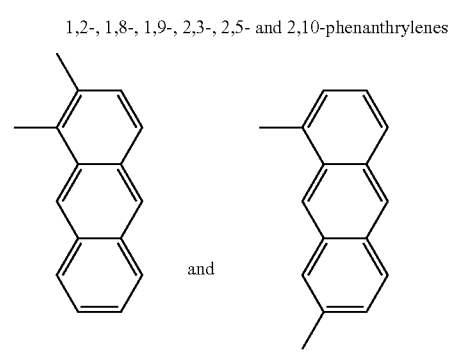 and 1,2- and 1,7-anthrylenes and any of these groups substituted by at least one monovalent substituting group, as above defined, in particular by a phenylketone group.

A second subset of kink-forming arylene units (Rb) is composed of optionally substituted arylene groups, the ends of which have a different direction, forming together an obtuse angle [kink-forming units (Rb-2)]. Non limitative examples of optionally substituted arylene groups the ends of which have a direction different from each other include:

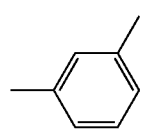

1,3-phenylene(or m-phenylene)

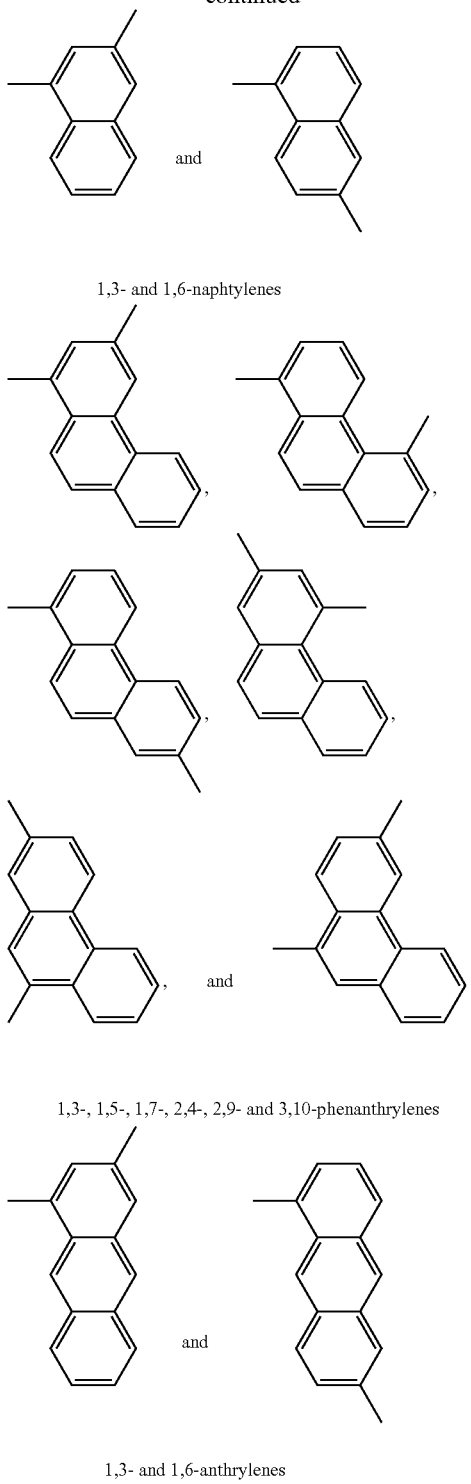

1,3- and 1,6-naphtylenes 1,3-, 1,5-, 1,7-, 2,4-, 2,9- and 3,10-phenanthrylenes 1,3- and 1,6-anthrylenes and any of these groups substituted by at least one monovalent substituting group, as above defined, in particular by a phenylketone group.

A third subset of kink-forming arylene units (Rb) is composed of optionally substituted arylene groups, the ends of which have the same direction and the same sense [kink-forming arylene units (Rb-3)]. Non limitative examples of optionally substituted arylene groups the ends of which the same direction and the same sense include:

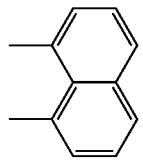

1,8-naphthylene

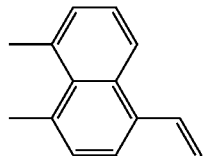

1,10- and 3,5-phenanthrylenes

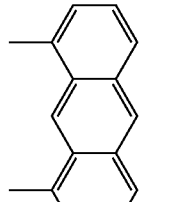

1,8- and 1,9-anthrylenes and any of these groups substituted by at least one monovalent substituting group, as above defined, in particular by a phenylketone group.

A fourth subset of kink-forming arylene units (Rb) is composed of optionally substituted arylene groups, the ends of which have the same direction, are of opposite sense and are disjoint [kink-forming arylene units (Rb-4)]. Non limitative examples of such optionally substituted arylene groups include:

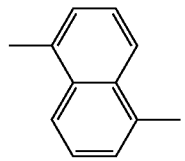 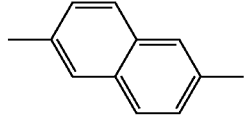

1,5- and 2,6-naphtylenes

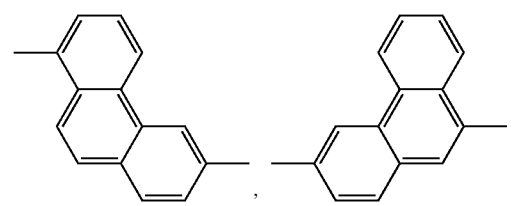

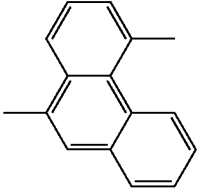

1,6-, 3,9- and 4,10-phenanthrylenes

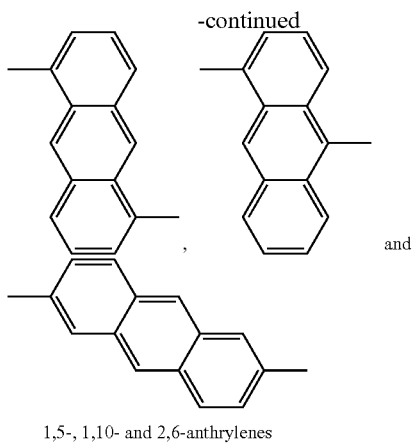

1,5-, 1,10- and 2,6-anthrylenes and any of these groups substituted by at least one monovalent substituting group, as above defined, in particular by a phenylketone group. Preferably, kink-forming arylene units (Rb) are chosen from kink-forming arylene units (Rb-1), kink-forming arylene units (Rb-2) and kink-forming arylene units (Rb-4). More preferably, kink-forming arylene units (Rb) are chosen from kink-forming arylene units (Rb-1) and kink-forming arylene units (Rb-2). Still more preferably, kink-forming arylene units (Rb) are chosen from kink-forming arylene units (Rb-1). Even still more preferably, kink-forming arylene units (Rb) are optionally substituted m-phenylenes.

Kink-forming arylene units (Rb), when contained in the polyarylene, result in more or less kinked polymer chains, exhibiting a higher solubility and fusibility than straight polymer chains. For this reason, such polyarylenes are commonly referred to as "kinked polymers".

The recurring units (R) of the kinked rigid-rod polyarylene (P) must be of a specific type, namely they must be a mix (M) consisting of:
  between 0 and 75 mole %, based on the total number of moles of recurring units (R), of rigid rod-forming arylene units (Ra), said rigid rod-forming arylene units (Ra) being optionally substituted by at least one monovalent substituting group
with
  between 25 and 100 mole %, based on the total number of moles of recurring units (R), of kink-forming arylene units (Rb), said kink-forming arylene units being optionally substituted or not by at least one monovalent substituting group.

The recurring units (R) are preferably a mix (M) consisting of:
  between 0 and 75 mole %, based on the total number of moles of recurring units (R), of rigid rod-forming arylene units (Ra) chosen from optionally substituted p-phenylenes,
with
  between 25 and 100 mole %, based on the total number of moles of recurring units (R), of kink-forming arylene units (Rb) chosen from (i) optionally substituted m-phenylenes and (ii) mixes of optionally substituted m-phenylenes with optionally substituted o-phenylenes.

Preferably, essentially all, if not all, the rigid rod-forming arylene units (Ra) of the mix (M) are p-phenylene units substituted by at least one substituting group. More preferably, essentially all, if not all, the rigid rod-forming arylene units (Ra) of the mix (M) are p-phenylenes substituted by at least one monovalent substituting group chosen from hydrocarbylketones [—C(=O)—R, where R is a hydrocarbyl group] and hydrocarbyloxyhydrocarbylketones [—C(=O)—R$^1$—O—R$^2$, where R$^1$ is a divalent hydrocarbon group and R$^2$ is a hydrocarbyl group], said hydrocarbylketones and hydrocarbyloxyhydrocarbylketones being themselves unsubstituted or substituted by at least one monovalent substituting group as those above listed. Still more preferably, essentially all, if not all, the rigid rod-forming arylene units (Ra) of the mix (M) are p-phenylenes substituted by at least one monovalent substituting group chosen from arylketones and aryloxyarylketones, said arylketones and aryloxyarylketones being unsubstituted or substituted by at least one monovalent substituting group as those above listed. Most preferably, essentially all, if not all, the rigid rod-forming arylene units (Ra) of the mix (M) are p-phenylenes substituted by an arylketone group, in particular by the phenylketone group.

Essentially all, if not all, the kink-forming arylene units (Rb) of the mix (M) are m-phenylene units optionally substituted by at least one substituting group. More preferably, essentially all, if not all, the kink-forming arylene units (Rb) of the mix (M) are m-phenylene units which are optionally substituted by at least one monovalent substituting group chosen from hydrocarbylketones [—C(=O)—R, where R is a hydrocarbyl group] and hydrocarbyloxyhydrocarbylketones [—C(=O)—R$^1$—O—R$^2$, where R$^1$ is a divalent hydrocarbon group and R$^2$ is a hydrocarbyl group], said hydrocarbylketones and hydrocarbyloxyhydrocarbylketones being themselves unsubstituted or substituted by at least one monovalent substituting group as those above listed. Still more preferably, essentially all, if not all, the kink-forming arylene units (Rb) of the mix (M) are unsubstituted m-phenylene units.

In the mix (M), the number of moles of the kink-forming arylene units (Rb), based on the total number of moles of the recurring units (R), is preferably of at least 30%, more preferably at least 35%, still more preferably at least 40% and most preferably at least 45%. On the other hand, in the mix (M), the number of moles of the kink-forming arylene units (Rb), based on the total number of moles of the recurring units (R), is preferably of at most 90%, more preferably at most 75%, still more preferably at most 65% and most preferably at most 55%.

Good results were obtained when the recurring units (R) were a mix consisting of p-phenylene units substituted by a phenylketone group with unsubstituted m-phenylene units, in a mole ratio of about 50:50.

The kinked rigid-rod polyarylene (P) may further comprise recurring units (R*), different from recurring units (R).

Recurring units (R*) may contain or not at least one strong divalent electron withdrawing group linked on each of its ends to an arylene group. Non limitative examples of recurring units (R*) free of such strong divalent electron withdrawing group are:

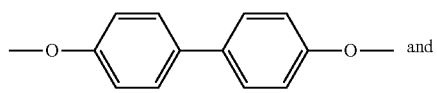  (1)

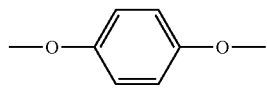  (2)

Recurring units (R*) contain preferably at least one strong divalent electron withdrawing group linked on each of its ends to an arylene group, in particular a p-phenylene group. The divalent electron withdrawing group is preferably chosen from the sulfone group [—S(=O)$_2$—], the carbonyl group [—C(=O)—], the vinylene group [—CH=CH—], the sulfoxide group [—S(=O)—], the azo group [—N=N—], saturated fluorocarbon groups like —C(CF$_3$)$_2$—, organic phosphine oxide groups [— P(=O)(=R$_h$)—, where R$_h$ is a hydrocarbyl group] and the ethylidene group [—C (=CA$_2$)-, where A can be hydrogen or halogen]. More preferably, the divalent electron withdrawing group is chosen from the sulfone group and the carbonyl group. Still more preferably, recurring units (R*) are chosen from:

(i) recurring units of formula

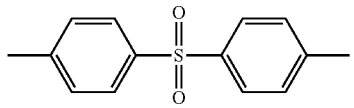
(3)

(ii) recurring units of formula

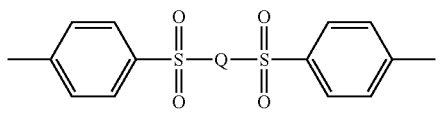
(4)

wherein Q is a group chosen from:

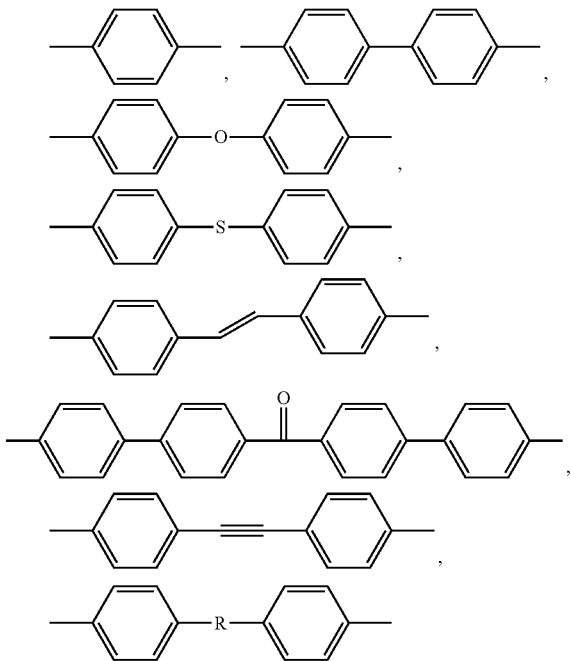

with R being:

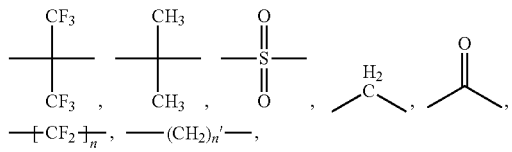

with n being an integer from 1 to 6 and n' being an integer from 2 to 6,

Q being preferably chosen from

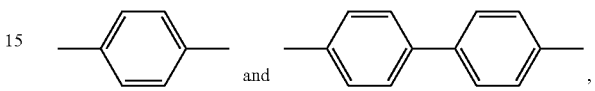

(iii) recurring units of formula

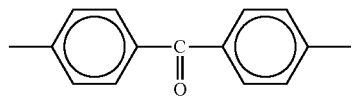
(5)

(iv) recurring units of formula

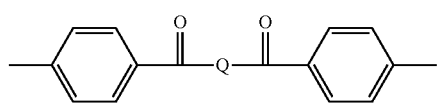
(6)

Preferably more than 75 wt. % and more preferably more than 90 wt. % of the recurring units of the polyarylene are recurring units (R). Still more preferably, essentially all, if not all, the recurring units of the polyarylene are recurring units (R).

Excellent results were obtained when the polyarylene was a kinked rigid-rod polyphenylene, essentially all, if not all, the recurring units of which consisted of a mix of p-phenylene substituted by a phenylketone group with unsubstituted m-phenylene in a mole ratio p-phenylene:m-phenylene of from 10:90 to 70:30, preferably of from 25:75 to 65:35, more preferably of from 35:65 to 60:40, still more preferably of from 45:55 to 55:45, and most preferably of about 50:50. Such a kinked rigid-rod polyphenylene is commercially available from Solvay Advanced Polymers, L.L.C. as PrimoSpire® PR-250 polyphenylene.

The kinked rigid-rod polyarylene (P) has usually a number average molecular weight greater than 1000, preferably greater than 5000, more preferably greater than about 10000 and still more preferably greater than 15000. On the other hand, the number average molecular weight of the kinked rigid-rod polyarylene is usually below 100000, and preferably below 70000. In a certain embodiment, the number average molecular weight of the kinked rigid-rod polyarylene is above 35000. In another embodiment, it is of at most 35000; in this embodiment, it is often of at most 25000 and sometimes of at most 20000. The number average molecular weight of a polyarylene in general, and in particular that of the kinked rigid-rod polyarylene (P), is advantageously determined by: (1) measuring a "relative" number average molecular weight of the polyarylene by Gel Permeation Chromatography (GPC) using polystyrene calibration standards, then (2) dividing the so-measured "relative" number average molecular weight by a factor 2. It is proceeded accordingly because the skilled in the art who is a specialist of polyarylenes knows that their "relative" number average molecular weight, as measured by GPC, are generally off by a factor of about 2 times; it has already been accounted for this correction factor in all the above cited lower and upper limits of molecular weight.

It can be amorphous (i.e. it has no melting point) or semi-crystalline (i.e. it has a melting point). It is preferably amorphous.

It has a glass transition temperature of advantageously above 50° C., preferably above 120° C. and more preferably above 150° C.

The kinked rigid-rod polyarylene (P) is generally unbranched. In particular, it is generally essentially free, or even free, of recurring branching units -Ary- $[ ]_x$ wherein Ary is a polyvalent arylene and x represents the number of bonds beyond two, x≥1.

The kinked rigid-rod polyarylene (P) can be prepared by any method. A method well known in the art to prepare such kinked rigid-rod polyarylene comprises polymerizing, preferably by reductive coupling, (i) at least one dihaloarylene molecular compound consisting of an optionally substituted rigid rod-forming arylene group, which is linked on each of its two ends to one halogen atom, such as chlorine, bromine and iodine, with (ii) at least one dihaloarylene molecular compounds consisting of an optionally substituted kink-forming arylene group, which is linked on each of its two ends to one halogen atom, such as chlorine, bromine, iodine, and fluorine. The elimination of the halogen atoms from the dihaloarylene molecular compounds results in the formation of respectively optionally substituted rigid rod-forming and optionally substituted kink-forming arylene groups.

Thus, for example:
- the elimination of both chlorine atoms from a molecule of p-dichlorobenzene, p-dichlorobiphenyl or their homologous of general formula Cl-$(\phi)_N$—Cl, N being an integer from 3 to 10, results in the formation of respectively 1, 2 or N adjacent p-phenylene units (rigid rod-forming arylene units); thus, p-dichlorobenzene, p-dichlorobiphenyl and their homologous of general formula Cl-$(\phi)_N$-Cl, N as above defined, can be polymerized, so as to form p-phenylene units;
- 2,5-dichlorobenzophenone (p-dichlorobenzophenone) can be polymerized, so as to form 1,4-(benzoylphenylene) units (also rigid rod-forming arylene units);
- m-dichlorobenzene can be polymerized, so as to form m-phenylene units (kink-forming arylene units).

In the present invention, one, two, three, or even more than three different kinked rigid-rod polyarylenes (P) can be used.

Optional Ingredients

The above described polymer material (M) may further contain one or more polymers other than the kinked rigid-rod polyarylene (P), and/or one or more non polymeric additives, collectively called optional ingredients.

The weight of the optional ingredients, based on the total weight of the material, ranges advantageously from 0 to 75 wt. %, preferably from 0 to 50 wt. %, more preferably from 0 to 25 wt. % and still more preferably from 0 to 10 wt. %, based on the total weight of the polymer material (M). Excellent results are obtained when the material is essentially free, or is even completely free, of said optional ingredients.

The non polymeric additives of concern include notably fibrous reinforcing agents, particulate fillers and nucleating agents such as talc and silica, adhesion promoters, compatibilizers, curing agents, lubricants, metal particles, mold release agents, organic and/or inorganic pigments like $TiO_2$ and carbon black, dyes, flame retardants, smoke-suppressing agents, heat stabilizers, antioxidants, UV absorbers, tougheners such as rubbers, plasticizers, anti-static agents, melt viscosity depressants, and mixtures thereof.

In a first particular embodiment, the polymer material (M) further comprises at least one polyarylene other than the kinked rigid-rod polyarylene (P). The polyarylene other than the kinked rigid-rod polyarylene (P) is preferably a kinked rigid-rod polyarylene (P2) of which more than 50 wt. % of the recurring units are recurring units (R2) of one or more formulae consisting of an optionally substituted arylene group, provided said optionally substituted arylene group is linked by each of its two ends to two other optionally substituted arylene groups via a direct C—C linkage, said recurring units (R2) being a mix (M2) consisting of:
  from 75 mole % to 100 mole %, based on the total number of moles of the recurring units (R2), of rigid rod-forming arylene units (R2a), said rigid rod-forming arylene units (R2a) being optionally substituted by at least one monovalent substituting group,
with
  from 0 to 25 mole %, based on the total number of moles of the recurring units (R2), of kink-forming arylene units (R2b), said kink-forming arylene units (R2b) being optionally substituted by at least one monovalent substituting group.

Unless stated otherwise, the kinked-rigid rod polyarylene (P2) meets advantageously all the characteristics of the kinked-rigid rod polyarylene (P) as above detailed, at any level of preference.

The amount of the recurring units (R2a) and (R2b) of the kinked-rigid rod polyarylene (P2), the number of moles of the kink-forming arylene units (R2b) in the mix (M2), based on the total number of moles of the recurring units (R2), is preferably of at least 1.0%, more preferably at least 5% and still more preferably at least 10%. On the other hand, in the mix (M2), the number of moles of the kink-forming arylene units (R2b), based on the total number of moles of the recurring units (R2), is preferably of at most 20%, and more preferably of at most 18%. Good results are obtained when the polyarylene (P2) is a kinked rigid-rod polyphenylene copolymer, essentially all, if not all, the recurring units of which consist of a mix (M2) of p-phenylene substituted by a phenylketone group with unsubstituted m-phenylene in a mole ratio p-phenylene:m-phenylene of from 80:20 to 95:5, preferably of from 80:20 to 90:10, and still more preferably of about 85:15. Such a kinked rigid-rod polyphenylene copolymer is commercially available from Solvay Advanced Polymers, L.L.C. as PrimoSpire® PR-120 polyphenylene.

In this first particular embodiment, the weight of the polyarylene (P2), based on the total weight of the polymer material (M), may be of at least 1%, at least 5%, of at least 10%, or at least 15%; on the other hand, the weight of the polyarylene (P2), based on the total weight of the material, may be of at most 99%, of at most 95%, of at most 75%, or of at most 60%.

In another particular embodiment, the polymer material (M) further comprises at least one thermoplastic polymer other than a polyarylene, selected from the group consisting of polyamides, polyether block amides, polyimides, polyetherimides, polyamideimides, polyarylethersulfones (such as polyphenylsulfones, bisphenol A polysulfones, polyethersulfones, polyetherethersulfones, polyethersulfoneimides and copolymers and mixtures thereof), polyetherketones, polyetheretherketones, polyetherketoneketones, polyarylene ethers [such as polyphenylene ethers and poly(2,6-dimethyl-1,4-phenylene ether)s], polyphenylene sulfides, polybenzimidazoles, polycarbonates, polyesters, polyurethanes, polyolefins, poly(methyl pentene)s, polytetrafluoroethylenes, polyethylenes, polypropylenes, liquid crystalline polymers, halogenated polymers, and copolymers and mixtures thereof.

In this particular embodiment, the polymer material (M) preferably further comprises at least one poly(aryl ether ketone) and, optionally in addition, at least one poly(aryl ether sulfone). As such, the polymer material (M) can meet any of the characteristics of the blends named "blend (B)" and "blend (T)" described in U.S. patent application Ser. No. 12/061,442, the whole content of which is herein incorporated by reference for all purposes, wherein the blend (B) comprises at least one kinked rigid-rod polyarylene (P) in a form other than fibers and at least one poly(aryl ether ketone), and the blend (T) comprises at least one kinked rigid-rod polyarylene (P), at least one poly(aryl ether ketone) and at least one poly(aryl ether sulfone). In particular, the polymer material (M) can be a blend (B) as previously described, wherein the poly(aryl ether ketone) is a polyetheretherketone (PEEK) homopolymer, essentially all the recurring units of which are of formula

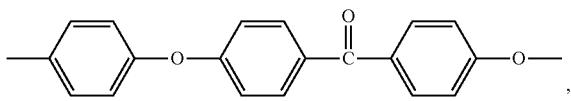

and wherein:
the weight of the kinked rigid-rod polyarylene (P), based on the total weight of the kinked rigid-rod polyarylene (P) and the poly(aryl ether ketone), can range from 30% to 70%, and the total weight of the kinked rigid-rod polyarylene (P) and the poly(aryl ether ketone), based on the total weight of the blend (B), can be above 80%.

The polymer material (M) can be also a blend (T) as previously described, wherein the poly(aryl ether ketone) is a polyetheretherketone (PEEK) homopolymer, essentially all the recurring units of which are of formula

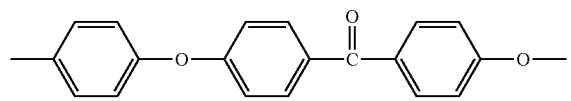

and the poly(aryl ether sulfone) is a polyphenylsulfone homopolymer (PPSU), essentially all the recurring units of which are of formula

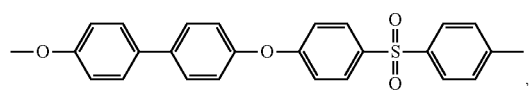

and wherein:
the weight of the kinked rigid-rod polyarylene (P), based on the total weight of the kinked rigid-rod polyarylene (P) and the poly(aryl ether ketone), can range from 30% to 70%, the poly(aryl ether sulfone) over kinked rigid-rod polyarylene (P) weight ratio can range from 0.15 to 0.50, the poly(aryl ether sulfone) over poly(aryl ether ketone) weight ratio can range from 0.15 to 0.50, and the total weight of the kinked rigid-rod polyarylene (P), the poly(aryl ether ketone) and the poly(aryl ether sulfone), based on the total weight of the blend (T), can be above 95%.

In another particular embodiment, the polymer material (M) comprises at least one kinked rigid-rod polyarylene (P) as above described, at least one kinked rigid-rod polyarylene (P2) as above described, at least one poly(aryl ether ketone) as above described, and optionally in addition, at least one poly(aryl ether sulfone) as above described.

In still another particular embodiment, to which the preference is generally not given, the polymer material (M) further contains at least one fibrous reinforcing agent, in particular an inorganic fibrous reinforcing agent such as glass fiber or carbon fiber, usually in an amount of from 10 to 50 wt. %, based on the total weight of the polymer material (M). This embodiment is generally not preferred because the neat polyarylene (P) has generally a high enough flexural and compression strength, and a high enough rigidity, and because the fibrous reinforcing agent generally impairs the ductility of the polymer material (M).

Biocompatibility Test Results

The biocompatibility of a polyarylene copolymer essentially all, if not all, the recurring units of which consisted of a mix of p-phenylene substituted by a phenylketone group with unsubstituted m-phenylene in a mole ratio p-phenylene:m-phenylene of about 50:50, commercially available from Solvay Advanced Polymers, L.L.C. as PRIMOSPIRE® PR-250 polyarylene, was tested using 4 standard tests covering cytotoxicity, sensitization, systemic toxicity and subacute (subchronic toxicity).

ISO Guinea Pig Maximization Sensitization test results:

Pellets of the polyarylene were extracted according to ISO 10993-12. The resulting extracts and control blanks were injected to different guinea pigs. On day 6, the dorsal site was reshaved and sodium lauryl sulfate in mineral oil was applied. On day 7, the animals were topically patched with the appropriate test extract and the corresponding blank animals were patched with the corresponding control blank. The patches were removed after 48±2 hours of exposure. Following a 2 week rest period, the animals were topically patched with the appropriate test extract and the corresponding blank animals were patched with the corresponding control blank. The patches were removed after 24±2 hours of exposure. The dermal patch sites were observed for erythema and edema 24±2 and 48±2 hours of exposure. Each animal was assessed for a sensitization response based upon the dermal scores. None of them elicit a sensitization response.

Minimum Essential Medium Elution Using L-929 Mouse Fibroblast Cells (ISO) (Cytotoxicity) Test Results:

Pellets of the polyarylene were extracted at 37±1° C. for 24-25 hours. The extract was inoculated onto the cell line and incubated at 37±1° C. in a humidified atmosphere with 5±1% $CO_2$ in the air. Cultures were evaluated for cytotoxic effects by microscopic observations after 24, 48 and 72 hours incubation periods. The polyarylene was considered non-toxic.

ISO Intracutaneous Reactivity Test:

Pellets of the polyarylene were extracted for 72±2 hours at 37±1° C. Two New Zealand white rabbits (*Oryctolagus cuniculus*) each received 5 sequential 0.2 mL intracutaneous injections along either side of the dorsal mid-line with the test extract on one side and the control extract on the other. The irritations reactions were scored at 24, 48 and 72 hours post-injection on each rabbit for evidence of erythema and edema. The polyarylene was considered as non-irritant.

ISO Acute Systemic Injection Test

Pellets of the polyarylene were extracted for 72±2 hours at 37±2° C. Groups of five albino, Swiss mice (*Mus musculus*) were injected systemically with test or control extracts at a dosing of 50 mL per kg body weight. The animals were observed for signs of toxicity immediately after injection and at 4, 24, 48 and 72 hours post injection. The polyarylene was considered non-toxic.

Should the disclosure of any of the patents, patent applications, and publications that are incorporated herein by reference conflict with the present specification to the extent that it might render a term unclear, the present specification shall take precedence.

The invention has been described with reference to various preferred and other embodiments but is not limited thereto. Those skilled in the art will appreciate that various modifications can be made without departing from the scope of the invention, which is defined by the following claims.

The invention claimed is:

1. A tubing comprising at least one kinked rigid-rod polyarylene of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix consisting of:
  between 0 and 75 mole %, based on the total number of moles of the recurring units (R), of rigid rod-forming arylene units (Ra), said rigid rod-forming arylene units (Ra) being optionally substituted by at least one monovalent substituting group, and
  between 25 and 100 mole %, based on the total number of moles of the recurring units (R), of kink-forming arylene units (Rb), said kink-forming arylene units (Rb) being optionally substituted by at least one monovalent substituting group;
wherein the tubing wall thickness is below 0.10 cm.

2. The tubing according to claim 1, wherein the tubing wall thickness is below 0.05 cm.

3. The tubing according to claim 1, wherein the tubing wall thickness is below 0.015 cm.

4. The tubing according to claim 1, wherein the tubing inner diameter is of at most 0.50 cm and the tubing outer diameter is of at most 0.80 cm.

5. The tubing according to claim 1, which is a needle comprising a body comprising at least one polymer material comprising the at least one kinked rigid-rod polyarylene, wherein said body extends along a longitudinal axis, has two ends and a hollow section all along the longitudinal axis, and at least one end of said body is beveled.

6. The tubing according to claim 5, wherein the tubing wall thickness is of at most 0.50 mm.

* * * * *